(12) United States Patent
Kuhr et al.

(10) Patent No.: US 6,294,392 B1
(45) Date of Patent: Sep. 25, 2001

(54) SPATIALLY-ENCODED ANALYTE DETECTION

(75) Inventors: Werner G. Kuhr, Oak Hills; Pankaj Singhal, Berkeley; Sara Ann Brazill, Diamond Bar, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/358,204

(22) Filed: Jul. 21, 1999

(51) Int. Cl.$^7$ ............................ G01N 33/543; C12Q 1/68
(52) U.S. Cl. .................................. 436/518; 435/6
(58) Field of Search ................... 435/6; 205/775; 436/44, 518

(56) References Cited

U.S. PATENT DOCUMENTS

| | | |
|---|---|---|
| 5,202,010 | 4/1993 | Guzman . |
| 5,312,527 | 5/1994 | Mikkelsen et al. . |
| 5,567,627 | 10/1996 | Lehnen . |
| 5,571,410 | 11/1996 | Swedberg et al. . |
| 5,607,646 * | 3/1997 | Okane et al. ................... 422/101 |
| 5,650,061 * | 7/1997 | Kuhr et al. ....................... 205/775 |
| 5,661,028 | 8/1997 | Foote . |
| 5,681,484 | 10/1997 | Zanzucchi et al. . |
| 5,699,157 | 12/1997 | Parce . |
| 5,700,642 | 12/1997 | Monforte et al. . |
| 5,726,404 | 3/1998 | Brody . |
| 5,741,639 | 4/1998 | Ensing et al. . |
| 6,007,775 * | 12/1999 | Yager et al. ....................... 422/57 |

FOREIGN PATENT DOCUMENTS

| | | |
|---|---|---|
| 9510344 | 4/1995 | (WO) . |
| 9911754 | 11/1999 | (WO) . |

OTHER PUBLICATIONS

Woolley et al., "Ultra–high–speed DNA fragment separations using microfabricated capillary array electrophoresis chips" Proc. Natl. Acad. Sci. USA vol. 91, pp. 11348–11352, 1994.*

Baba, Y. (1996) "Capillary Affinity Gel Electrophoresis" *Mol. Biotech.* 6:143–153.

Baba, Y. et al. (1998) "Base–specific Separation of Oligodeoxynucleotides by Capillary Affinity Gel Electrophoresis," *Electrophoresis* 19:433–436.

Guttman, A. and Cooke, N. (1991) "Capillary Gel Affinity Electrophoresis of DNA Fragments," *Anal. Chem.* 63:2038–2042.

Ozaki, Y. et al. (1997) "Affinity Capillary Electrophoresis Using DNA Conjugates," *Nucleic Acids Symposium Series* 37:235–236.

Qian X. and Tomer, K. (1998) "Affinity Capillary Electrophoresis Investigation of an Epitope on Human Immunodeficiency Virus Recognized by a Monoclonal Antibody," *Electrophoresis* 19:415–419.

Rippel, G. et al. (1997) "Affinity Capillary Electrophoresis," *Electrophoresis* 18:2175–2183.

* cited by examiner

*Primary Examiner*—John S. Brusca
*Assistant Examiner*—Jeffrey S. Lundgren
(74) *Attorney, Agent, or Firm*—The Law Offices of Johnathan Alan Quine; Tom Hunter

(57) ABSTRACT

A flow-through microchannel (e.g. capillary) biosensor is described for the for the detection of multiple, different analytes (e.g. nucleic acids, proteins, sugars, etc.) targets in a sample by binding them to "complementary" binding partners (e.g. complementary nucleic acids, ligands, antibodies, etc.). The binding partners are immobilized in different sections of a microchannel (e.g. a fused silica capillary). After fabrication of the biosensor, a sample is flushed through the capillary, and any target analyte(s) contained within the sample are bound to the immobilized binding partner(s) on the microchannel wall forming bound complexes. Finally, the bound complexes are simultaneously denatured along the entire length of the capillary and flushed out past a detector poised downstream, and the analyte concentration is measured (e.g., using sinusoidal voltammetry). Direct electrochemical detection of underivatized DNA is accomplished by oxidizing its sugar backbone and the amine containing nucleobase at the copper electrode. The elution time of the desorbed target DNA(s) is used for the sequence identification of the target. Multiple genetic sequences can be diagnosed by using a single biosensor in this manner. The sensor is highly specific due to hybridization chemistry, and extremely sensitive due to electrochemical detection.

24 Claims, 9 Drawing Sheets

Capillary DNA-biosensor with TB+HIV Probes Immobilized.
Length of each probe zone = 1 cm. Distance between zones = 7 inches
Elution of Target with TBE buffer, pH = 11, after 30 minute incubation
Detection: Sinusoidal voltammetry with 40 μm Copper electrode
2 Hz, 0-700 mVp-p sine wave. Response shown at 5th Harmonic.

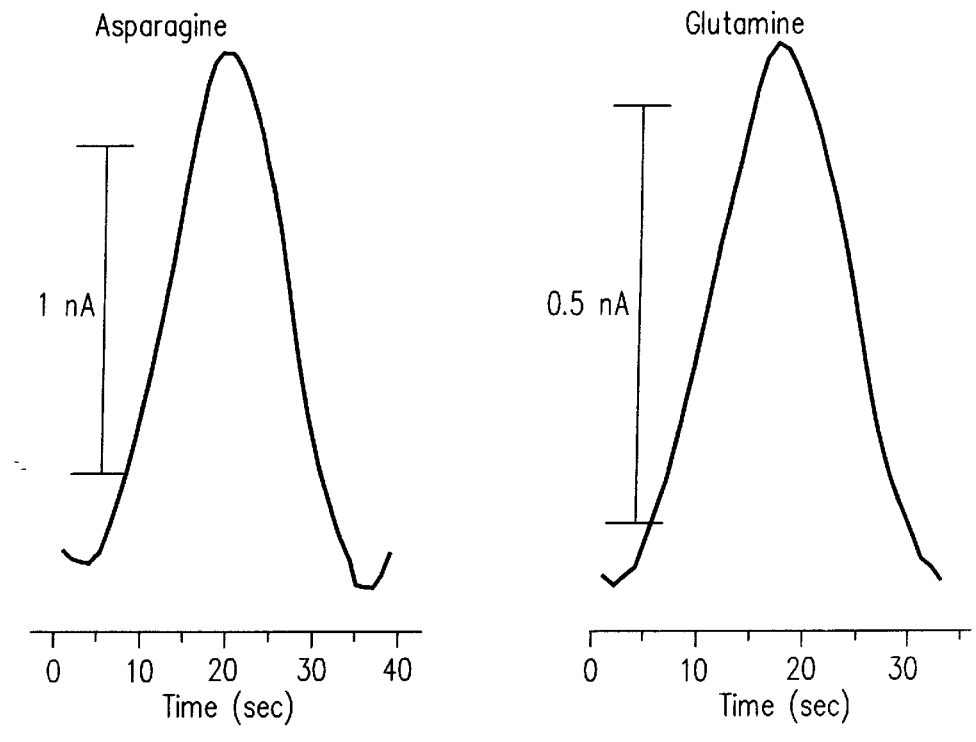
FIG. 10A
FIG. 10B
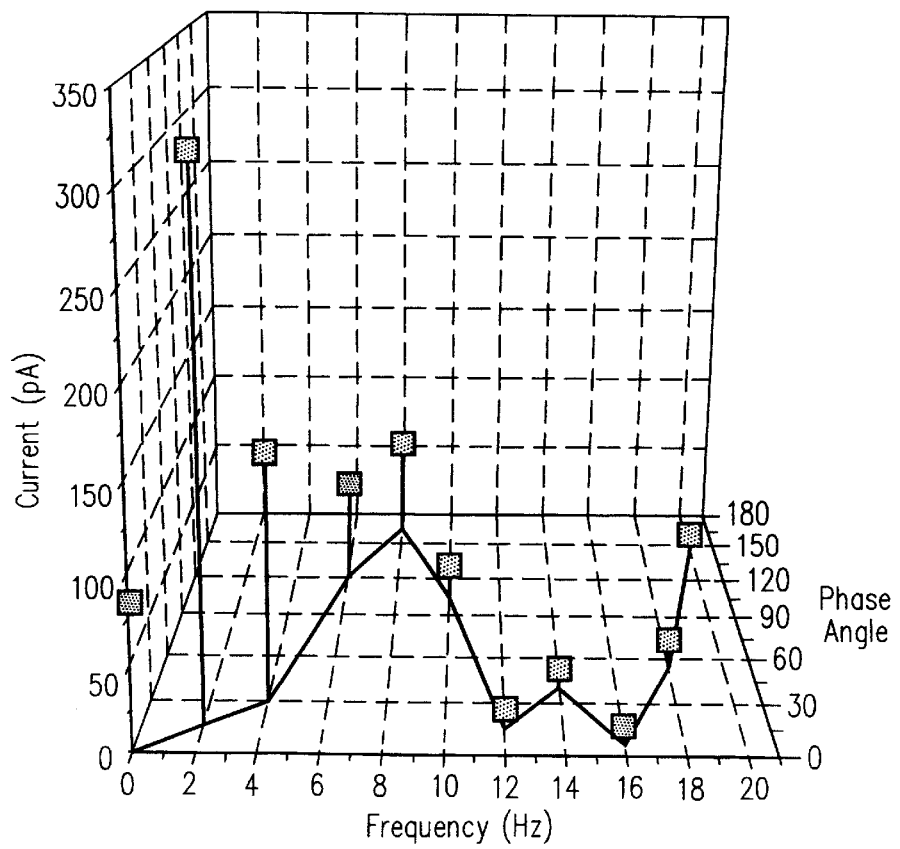
FIG. 11

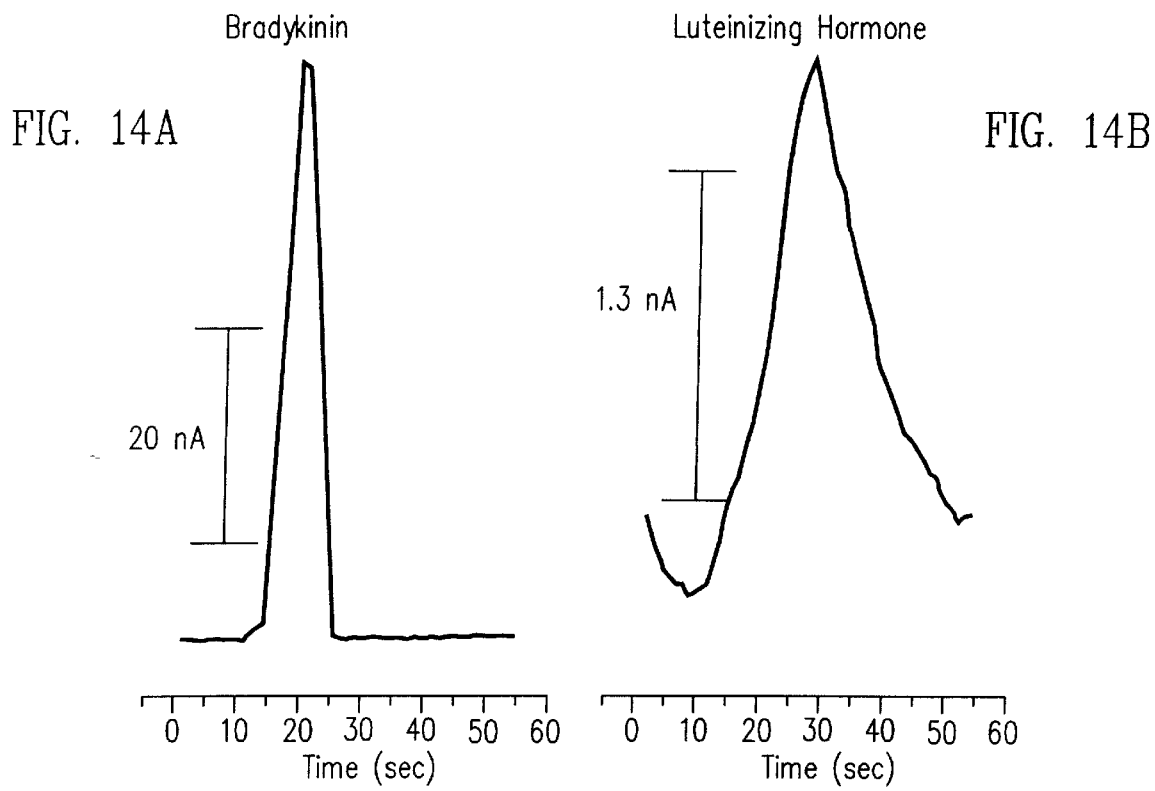
FIG. 14A  Bradykinin
FIG. 14B  Luteinizing Hormone
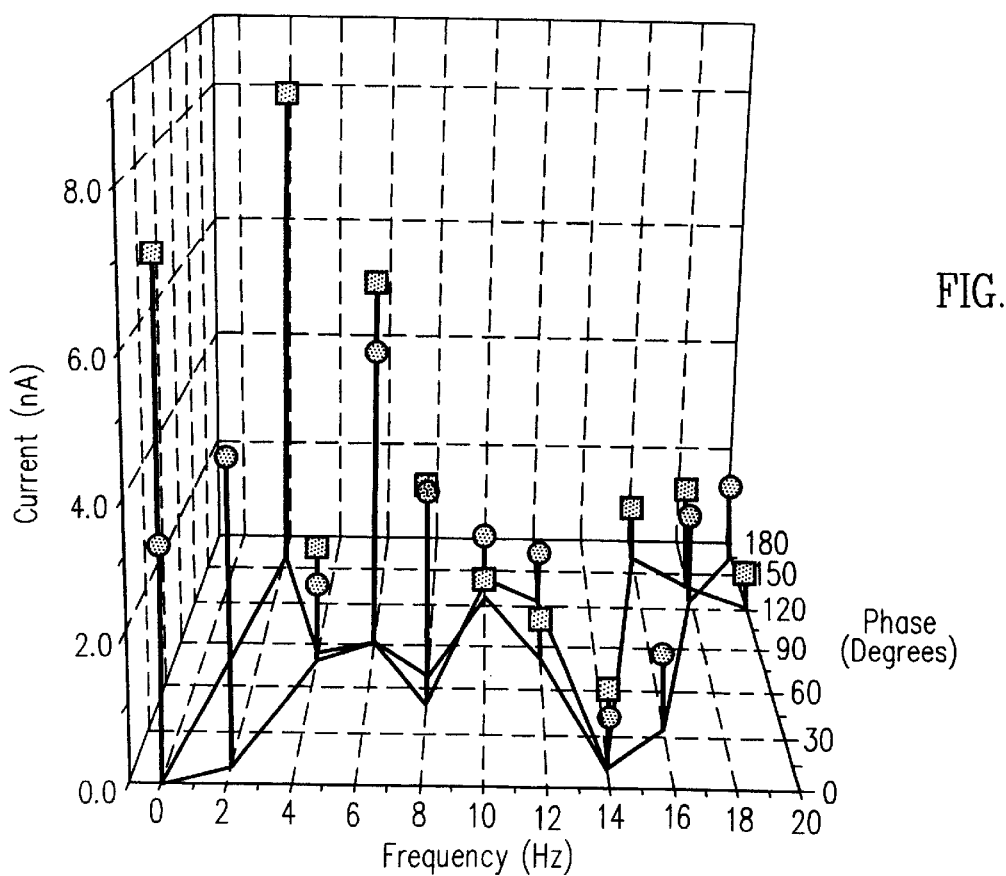
FIG. 15

SPATIALLY-ENCODED ANALYTE DETECTION

STATEMENT AS TO RIGHTS TO INVENTIONS MADE UNDER FEDERALLY SPONSORED RESEARCH AND DEVELOPMENT

This work was supported by the National Institutes of Health (GM44112-01A1) and the UC BioSTAR project. The Government of the United States of America may have certain rights in this invention.

CROSS-REFERENCE TO RELATED APPLICATIONS

Not Applicable

FIELD OF THE INVENTION

This invention relates to the field of diagnostics. In particular this invention provides devices and methods that allow rapid detection and/or quantitation of multiple analytes and yet does not require the use of labels or labeling steps.

BACKGROUND OF THE INVENTION

Immunoassays and nucleic acid hybridization chemistries are rapidly being developed towards the goal of detecting genetic defects, performing disease diagnostics, and performing prognostic evaluations (Sosnowski et al. (1997) *Proc. Natl. Acad. Sci. USA*, 94: 1119–1123). Antibodies, nucleic acid binding proteins, receptor ligands, and nucleic acids are known to bind very specifically and with high efficiency to their congnate "binding partner" under suitable conditions. This phenomenon is frequently used for the recognition and diagnosis of disease-causing organisms (e.g., HIV), pathological conditions (e.g. cancer, liver disease, kidney disease, degenerative joint disease, etc.), substance abuse (e.g. detection of products such as cotinine, etc.), and the like.

Numerous disease markers, and pathogen markers (e.g. proteins and/or nucleic acids) are well known and have been thoroughly characterized. Thus, binding partners (e.g. nucleic acids, antibodies, and the like), that specifically bind such markers can be synthesized and/or isolated and used as markers for recognition of the disease state, or disease-causing agent (Landegren et al. (1988) *Science*, 242: 229, Mikkelson (1996) *Electroanalysis*, 8: 15–19). Various assays are carried out routinely in microbiology laboratories or pathology laboratories using such methodologies.

Nucleic acid hybridization, antibody binding reactions, protein binding reactions, and lectin binding reactions are generally detected through the use of labels that either intercalate into the molecule (e.g. into the double helix of a DNA) or are covalently attached to either the target or the probe molecule (see, e.g., Sosnowski et al. (1997) *Proc. Natl. Acad. Sci. USA*, 94: 1119–1123, LePecq and Paoletti (1966) *Anal. Biochem.*, 17: 100–107, Kapuscinski and Skoczylas (1977) *Anal. Biochem.*, 83: 252–257). In some cases, electrogenerated chemiluminescence has also been utilized to detect an intercalated electroactive luminescent marker (Pollard-Knight et al. (1990) *Anal. Biochem.*, 185: 84–89, Pollard-Knight et al.(1990) *Anal. Biochem.*, 185: 353–358, Tizard et al. (1990) *Proc. Natl. Acad. Sci. USA*, 12: 4514–4518). All of these detection strategies require the derivatization of the target or probe molecule, either before (e.g. for covalent labeling) or after (e.g. for intercalation or indirect labeling) the binding reaction between the probe and target molecule. This introduces contamination problems. In addition, where multiple analytes are analyzed simultaneously multiple labels must be employed. In addition, tedious sample handling is required which further enhances the risk of contamination and/or leads to false analysis. These and other problems are overcome by the present invention.

SUMMARY OF THE INVENTION

This invention provides novel devices and methods for detecting and/or quantifying a plurality of analytes in a sample. This invention provides a flow-through microfluidic (e.g., capillary) biosensor for detecting different target analytes (e.g. nucleic acids) in a sample after binding to their cognate "binding partners" (e.g. nucleic acids, antibodies, lectins, etc.). In general, binding partner "probes", specific to various analytes are immobilized in different sections of a capillary channel, e.g. using photolabile biotin/avidin technology. The sample is then flushed through the capillary, so that the target analytes are bound to the binding partners (capture agents) immobilized on the capillary wall and the rest of the sample is eluted from the capillary. Finally, the complexed (bound) analyte is released along the entire length of the channel and flushed past a detector. In a preferred embodiment, the desorbed, target-analytes are detected at a copper electrode poised downstream using sinusoidal voltammetry (Singhal and Kuhr (1997) *Anal. Chem.*, 69: 3552–3557, Singhal et al. (1997) *Anal. Chem.*, 69: 1662–1668). The time from the elution of the target analyte(s) to detection is used to determine the identity of each analyte. Multiple analytes, of the same species of molecule (e.g., all nucleic acids), or of different species (e.g. proteins and nucleic acids), can be diagnosed by using a single biosensor in this manner. The sensor is highly specific due to the use of specific binding partners, and extremely sensitive due to electrochemical detection.

Thus, in one embodiment, this invention provides devices for detecting a two or more analytes in a sample. The devices comprise a channel having affixed therein a binding partner for each of the two or more analytes, where the binding partners for each of the two or more analytes are located in different regions of the channel and the channel has a cross-sectional area small enough such that when analytes are released from the two or more binding partners into a fluid flowing through the channel, the analytes remain spatially segregated until they reach a detection point along, or at the end of, the channel downstream from the binding partners; and a detector that detects the analytes at the detection point.

The channel can be any convenient channel, e.g. a capillary tube, a capillary electrophoresis tube, a channel etched in a surface, a channel formed by hydrophobic agents printed onto a surface, etc. The channel can have essentially any dimension(s) as long as the analytes remain sufficiently segregated to be distinguished when they reach a detection region in the channel or at the channel end. Preferred channels have a cross-sectional area that provides a Renold's number (Re) of less than about 1. Preferred channels have a cross-sectional diameter or width less than or equal to about 500 $\mu$m, more preferably less than or equal to about 100 $\mu$m, and most preferably less than or equal to about 50 $\mu$m. In particularly preferred devices the two or more target analytes comprise at least three, preferably at least 4, more preferably at least 5, and most preferably at least 10, at least 50, at least 100, or at least 500 different analytes (and hence that many different binding partners). A wide variety of binding partners are suitable including, but not limited to antibodies, binding proteins, and nucleic acids. Similarly many detectors are suitable and include spectrophotometers (e.g. absorbance spectrophotometers), and electroanalytic detectors (including essentially any amperometric and/or voltammetric and/or potentiometric and/or coulometric detectors). Preferred detectors include voltammeters, especially a sinusoidal voltammeters.

In another embodiment, this invention provides methods of detecting two or more target analytes in a sample. The methods involve providing a detection device as described herein; ii) passing a fluid comprising a sample through the channel under conditions where the target analytes present in the fluid bind to their respective binding partners thereby spatially encoding the analytes along the channel; iii) releasing the analytes from the binding partners into fluid flow passing along the channel; and iv) detecting the analytes at a position along the channel downstream from the binding partners. In preferred methods, the analytes are not labeled. In particularly preferred embodiments the analytes are not labeled. In particularly preferred devices the two or more target analytes comprise at least three, preferably at least 4, more preferably at least 5, and most preferably at least 10, at least 50, at least 100, or at least 500 different analytes (and hence that many different binding partners are present in the channel(s) comprising the detection device). In some preferred embodiments, the fluid flow induced by a pressure difference and/or by electroosmotic flow. fluid flow. Preferred "sample" fluids for the detection of analytes include blood, plasma, serum, urine, oral fluid, cerebrospinal fluid, and lymph. Detecting can be by a variety of means including spectrophotometers (e.g. absorbance spectrophotometry), and electroanalytic methods (including essentially any amperometric and/or voltammetric and/or potentiometric and/or coulometric method). Preferred detection methods voltammetry, especially sinusoidal voltammetry. In particularly preferred methods, the analytes are nucleic acids and the detecting detects target analytes at a concentration of less than $1 \times 10^{-9}$ M.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "antibody", as used herein, includes various forms of modified or altered antibodies, such as an intact immunoglobulin, an Fv fragment containing only the light and heavy chain variable regions, an Fv fragment linked by a disulfide bond (Brinkmann et al. (1993) *Proc. Natl. Acad. Sci. USA*, 90: 547–551), an Fab or (Fab)'2 fragment containing the variable regions and parts of the constant regions, a single-chain antibody and the like (Bird et al. (1988) *Science* 242: 424–426; Huston et al. (1988) Proc. Nat. Acad. Sci. USA 85: 5879–5883). The antibody may be of animal (especially mouse or rat) or human origin or may be chimeric (Morrison et al. (1984) *Proc Nat. Acad. Sci. USA* 81: 6851–6855) or humanized (Jones et al. (1986) *Nature* 321: 522–525, and published UK patent application #8707252).

The terms "binding partner", or "capture agent", or a member of a "binding pair" refers to molecules that specifically bind other molecules to form a binding complex such as antibody-antigen, lectin-carbohydrate, nucleic acid-nucleic acid, biotin-avidin, etc.

The term "specifically binds", as used herein, when referring to a biomolecule (e.g., protein, nucleic acid, antibody, etc.), refers to a binding reaction which is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The term channel refers to a path that directs fluid flow in a particular direction. The channel can be formed as a groove or trench having a bottom and sides, or as a fully enclosed "tube". In some embodiments, the channel need not even have "sides". For example, a hydrophobic polymer can be applied to a flat surface and thereby confine and/or direct fluid flow on that surface in a narrow (e.g. hydrophilic) domain. The channel preferably includes at least one surface to which a binding partner (capture) agent can be affixed.

A "target analyte" is any molecule or molecules that are to be detected and/or quantified in a sample. Preferred target analytes include biomolecules such as nucleic acids, antibodies, proteins, sugars, and the like.

The term "microchannel" is used herein for a channel having dimensions which provide low Reynolds number operation (Re$\leq$1, preferably Re$\leq$0.1, more preferably Re$\leq$0.01, and most preferably Re$\leq$0.001). Generally low Reynolds number operation, fluid dynamics are dominated by viscous forces rather than inertial forces.

The term capillary tube refers to a tube of narrow dimension (e.g. typically providing low Re flow). Open-ended capillary tubes, when contacted with water will typically uptake the water by capillary action. Capillary tubes can be fabricated of a number of materials including, but not limited to, glass, plastic, quartz, ceramic, and various silicates.

A "capillary electrophoresis tube" refers to a "capillary tube" typically used or intended to be used in a capillary electrophoresis device.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111 :2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters. An extensive guide to the hybridization of nucleic acids is found in, e.g., Tijssen (1993) *Laboratory Techniques in Biochemistry and Molecular Biology— Hybridization with Nucleic Acid Probes* part I, chapt 2, *Overview of principles of hybridization and the strategy of nucleic acid probe assays*, Elsevier, N.Y. (Tijssen). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1–3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

"Spatial segregation" refers to the differences in the localization of a the concentration distributions of two or more species of molecule (e.g. analytes) in a fluid stream. Where the analytes are spatially segregated (i.e., flow encoded) it is possible to detect distinct signals for each analyte of interest even though the type of signal for all of the analyte may be identical. Thus, the analyte identity can be determined by position along the "flow path" or time of detection, and differences in labels associated with each analyte are not required.

Electroanalytic methods refer to methods that exploit the "electrical" properties (e.g., resistance, conductance, capacitance, impedance, etc.) of a system or analyte to extract information regarding that system. Electroanalytic methods include, essentially any amperometric and/or voltammetric and/or potentiometric and/or coulometric method. Preferred electroanalytic methods include cyclic voltammetry, ac, dc, or rotating ring-disc voltammetry, sinusoidal voltammetry, impedance spectroscopy, and the like.

The term "sinusoidal voltammetry" refers to the use of a large amplitude sinusoidal potential waveform which is used in analogous fashion t cyclic voltammetry (see, e.g., U.S. Pat. No. 5,650,061).

BRIEF DESCRIPTION OF THE DRAWINGS

FIGS. 10A and 10B show the sinusoidal time domain response of asparagine and glutamine at the sixth harmonic (12 Hz). FIG. 10A shows 10 μM asparagines, while FIG. 10B shows 10 μM glutamine.

FIG. 11 shows the background subtracted frequency domain spectrum for 10 μM Insulin B-chain.

FIG. 13 shows 10 μM Luteininzing Hormone, while FIG. 13 shows 10 μM Bradykinin.

FIGS. 14A and 14B show the time domain response of Bradykinin and Luteinizing Hormone-Releasing Hormone at the second harmonic (4 Hz), respectively.

FIG. 15 shows the background subtracted frequency domain response for Neurotensin and Substance P, respectively.

DETAILED DESCRIPTION

Figure 1:
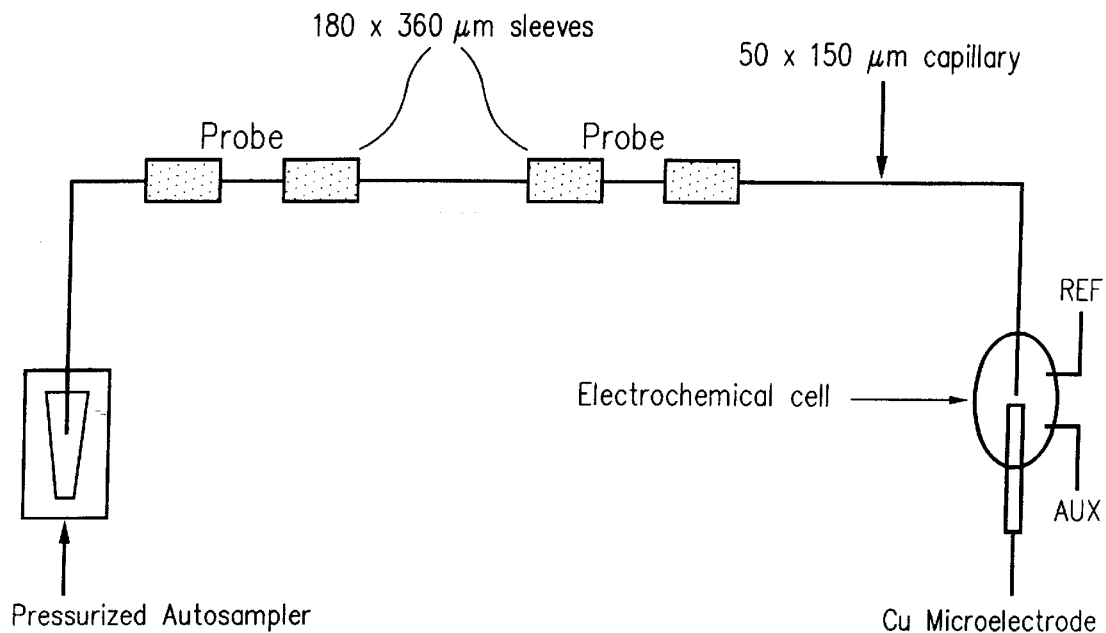
FIG. 1 shows a schematic of a capillary based DNA-biosensor with electrochemical detection. Two different probe sections are present in the capillary; probe 1, a TB-specific probe, and probe 2, an HIV-specific probe. An HPCE autosampler is used for various stringent washes and rinses required for specific-hybridization of complementary DNA-targets to these immobilized probes. A copper electrode is positioned at outlet of the capillary biosensor by using a machined two-part system.

I. Methods for Efficient Detection of Multiple Analytes

This invention provides novel methods and instruments for the rapid detection and/or quantification of multiple analytes in a sample. In one preferred embodiment, this invention comprises a channel having attached therein binding partner(s) specific for the analytes that it is desired to detect. Different binding partners are located in different regions of the channel so that when the analyte(s) are bound they are "spatially encoded" by their location along the channel. The bound analytes are subsequently released from the binding partner, or the binding partner/analyte complex is released from the wall of the channel, into a fluid flowing through the channel. The channel dimensions are such that the analytes remain spatially segregated until they reach a detection point in the channel downstream from said binding partners.

When the analytes or analyte/binding partner complexes are released into the flow, they are spatially encoded; their position in the stream relative to each other being dependent on the position of the binding partners when they were affixed to the channel wall(s). The time difference between the release and the detection can therefore be used to specifically identify the particular analyte generating (or not generating) an output signal.

Because the analytes can each be specifically identified without the use of a label to distinguish them from other analytes numerous and tedious sample-handling and labeling steps are eliminated. This eliminates multiple labeling and contamination problems. Also, the risk of sample contamination, that could lead to an elevated incidence of false positives is reduced or eliminated.

It is noted that the channels can be prepared well before use and different microfluidic structures (e.g. channels) can be swapped into and out of the device that provides sample handling, fluid flow and analyte detection. Different channels can be provided for different collections of analytes and multiple channels, either the same or different, can be run simultaneously.

The methods and devices of this invention are therefore well suited to the detection of analytes in a clinical setting. The ability to detect underivatized analytes (e.g. DNA, mRNA, etc.) greatly simplifies the procedure and helps in preventing sample contamination and false identification problems.

In one particularly preferred embodiment, the use of copper electrodes with sinusoidal voltammetry overcomes many of the problems encountered by traditional electrochemical measurements, and thereby allows the detection of the analyte. The sensitivity of the detection strategy is due to the effective decoupling of the faradic signal from the capacitive background currents in the frequency domain. Thus, for example, ssDNA and dsDNA can be detected in the picomolar concentration range, and the electrochemical signal is due to the oxidation of easily accessible sugars on the outer perimeter of the DNA double helix compared to a ssDNA of the same size.

A sensor that can detect multiple targets by using only one detector provides a cheaper and more compact detection system that is also easier to fabricate.

II. System Components

A) Channel

1) Channel Types and Dimensions

Virtually any type of channel is suitable for the practice of the present invention so long as the channel allows the passage of materials through it without substantial mixing between components in a solution at different positions along the channel. In other words, in a preferred capillary, analytes (or other detectable reagents) initially released at distinct locations along the channel remain spatially segregated at a detection point "downstream" from the initial release point. Spatial segregation refers to the ability to detect distinct signals for each analyte of interest even though the type of signal for all of the analyte may be identical. Thus, the analyte identity can be determined by position along the "flow path" or time of detection, and differences in labels associated with each analyte are not required.

Spatial segregation, however, does not require complete segregation of the analytes away from each other. To the contrary, there can exist significant overlap and peak concentrations can be detected and, associated concentration profiles and be measured and/or calculated to provide positive/negative detection and/or full analyte quantification.

Particularly preferred channels for use in this invention are "microchannels". The term microchannel is used herein for a channel having dimensions that provide low Reynolds number operation, i.e., for which fluid dynamics are dominated by viscous forces rather than inertial forces. Reynolds number, sometimes referred to the ratio of inertial forces to viscous forces is given as:

$$Re = \rho d^2/\eta \tau + \rho u d/\eta$$

where u is the velocity vector, $\rho$ is the fluid density, $\eta$ is the viscosity of the fluid, d is the characteristic dimension of the channel, and $\tau$ is the time scale over which the velocity is changing (where $u/\tau=\delta u/dt$). The term "characteristic dimension" is used herein for the dimension that determines Reynolds number, as is known in the art. For a cylindrical channel it is the diameter. For a rectangular channel, it depends primarily on the smaller of the width and depth. For a V-shaped channel it depends on the width of the top of the "V", and so forth. Calculation of Re for channels of various morphologies can be found in standard texts on fluid mechanics (e.g. Granger (1995) *Fluid Mechanics*, Dover, N.Y.; Meyer (1982) *Introduction to Mathematical Fluid Dynamics*, Dover, N.Y.).

Fluid flow behavior in the steady state ($\tau \rightarrow$infinity) is characterized by the Reynolds number, Re=$\rho u d/\eta$. Because of the small sizes and slow velocities, microfabricated fluid systems are often in the low Reynolds number regime (Re less than about 1). In this regime, inertial effects, that cause turbulence and secondary flows, and therefore mixing within the flow, are negligible and viscous effects dominate the dynamics. Under these conditions, flow through the channel is generally laminar.

Since the Reynolds number depends not only on channel dimension, but on fluid density, fluid viscosity, fluid velocity and the timescale on which the velocity is changing, the absolute upper limit to the channel diameter is not sharply defined. In fact, with well designed channel geometries, turbulence can be avoided for R<100 and possibly for R<1000, so that high throughput systems with relatively large channel sizes are possible. The preferred channel characteristic dimension range is between about 0.5 $\mu$m and 100 mm. Particularly preferred channel range from a characteristic dimension of about 1 $\mu$m to about 100 $\mu$m, most preferably from about 5 $\mu$m to about 100 $\mu$m. A more preferred range is between about 5 $\mu$m and 50 $\mu$m.

The devices of this invention need not be confined to low Reynolds number operation. Where the binding probes are widely separated and hence the released analytes are widely separated in the flow considerable convective mixing can occur in the channel without the different analytes "overlapping" and masking each other's signal. In addition, it will be appreciated that considerable mixing of the two analytes can occur and as long as there is a significant (e.g., statistically significant) spatial separation between the peak concentrations of the two analytes, the signals will be distinguishable and detection of each analyte can be effected. However, as analytes co-mix, quantification of each individual analyte may become progressively more difficult. Nevertheless, even in this context quantification can be obtained by estimating or modeling the spatial distribution of the analyte based on the location of the concentration peak(s) and the rate of fall-off to provide an approximation of the integrated signal for each analyte.

As indicated above, any channel configuration is suitable so long as the mixing requirements described above are met. Thus, appropriate channels include, but are not limited, to channels formed by opposed barriers, open-topped grooves, closed channels, and the like. The channels can have virtually any cross-section, e.g. circular, square, rectangular, triangular v-shaped, u-shaped, hexagonal, octagonal, irregular, and so forth. The channel(s) used in this invention also need not be continuous. Thus, for example, channels can be formed by an aggregation of porous particles, by mixed or cross-linked polymers, and so forth.

Any channel material is suitable for practice of this invention so long as the material is essentially stable to the solutions passed through it. Preferred materials are capable of binding, or being derivatized to bind, to the binding partner or a linker to the binding partner. In addition, in a preferred embodiment, the material is selected and/or modified so that it does not substantially bind to the analyte. Preferred materials also do not bind, or otherwise interact with the probes in regions other than where it is desired to affix the probes.

Particularly preferred materials include, but are not limited to glass, silicon, quartz or other minerals, plastic(s), ceramics, metals, paper, metalloids, semiconductive materials, cements, and the like. In addition, substances that form gels, such as proteins (e.g., gelatins), lipopolysaccharides, silicates, agarose and polyacrylamides can be used. A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like.

In the case of conductive or semiconductive substrates, there is preferably an insulating layer on the substrate. This is particularly important where the device incorporates electrical elements (e.g. electrical fluid direction systems, sensor, and the like or uses electroosmotic forces to move materials about the system). In the case of polymeric substrates, the substrate materials may be rigid, semi-rigid, or non-rigid, opaque, semi-opaque, or transparent depending upon the use for which they are intended. For example, devices that include an optical or visual detection element are generally fabricated, at lease in part, from transparent materials to allow or at least facilitate that detection. Alternatively, transparent windows of e.g. glass or quartz can be incorporated into the device for these types of detection elements. Additionally, the polymeric materials may have linear or branched backbones and may be crosslinked or noncrosslinked. Example of particularly preferred polymeric materials include e.g. polydimethylsiloxanes (PDMS), polyurethane, polyvinylchloride (VPC), polystyrene, polysulfone, polycarbonate, and the like.

It will be appreciated that the channel can be a component of a larger object. Thus, the channel can be assembled with one or more other channels to provide a multiplicity of channels whereby a number of different assays can be run simultaneously. The channel can be a component of an instrument that includes appropriate liquid handling, and/or detection, and/or sample processing/application functions.

The channel(s) can also be fabricated as a as a reusable or disposable unit that can be conveniently "plugged" into an instrument for running the assays of this invention. It will be appreciated that the channel(s) can be provided on any one or more of a wide variety of objects including, but not limited to a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead.

In particularly preferred embodiments, one or more channels are provided as a capillary tube (e.g. a capillary electrophoresis tube), on a glass or silicon slide, as a capillary channel, or fabricated as an element of an "integrated circuit" having on board circuit elements for control of liquid flow, sample application, and/or signal detection. In a most preferred embodiment, the channel is provided as a capillary tube, e.g. a capillary electrophoresis tube as illustrated herein in the Examples.

2) Channel Fabrication

Methods of fabricating the channels of this invention are well known to those of skill in the art. For example, where the channel is formed of one or more capillary tubes, the capillaries can be purchased from commercial vendors (e.g. Polymicron Technologies, Tucson, Ariz.) or pulled or extruded by conventional capillary "pulling" machines.

Where the channels are fabricated on a surface, they can be formed using standard techniques, e.g. they can be machined, molded, carved, etched, laminated, extruded, or deposited, etc.

In one preferred embodiment, the channel(s) are fabricated using micromachining processes (e.g. photolithography) well known in the solid state electronics industry. Commonly, microdevices, e.g. microchannels, are constructed from semiconductor material substrates such as crystalline silicon, widely available in the form of a semi-conductor wafer used to produce integrated circuits, or from glass. Because of the commonality of material(s), fabrication of microdevices from a semiconductor wafer substrate can take advantage of the extensive experience in both surface and bulk etching techniques developed by the semiconductor processing industry for integrated circuit (IC) production.

Surface etching, used in IC production for defining thin surface patterns in a semiconductor wafer, can be modified to allow for sacrificial undercut etching of thin layers of semiconductor materials to create movable elements. Bulk etching, typically used in IC production when deep trenches are formed in a wafer using anisotropic etch processes, can be used to precisely machine edges or trenches in microdevices. Both surface and bulk etching of wafers can proceed with "wet processing", using chemicals such as potassium hydroxide in solution to remove non-masked material from a wafer. For microdevice construction, it is even possible to employ anisotropic wet processing techniques that rely on differential crystallographic orientations of materials, or the use of electrochemical etch stops, to define various channel elements.

Another etch processing technique that allows great microdevice design freedom is commonly known as "dry etch processing". This processing technique is particularly suitable for anistropic etching of fine structures. Dry etch processing encompasses many gas or plasma phase etching techniques ranging from highly anisotropic sputtering processes that bombard a wafer with high energy atoms or ions to displace wafer atoms into vapor phase (e.g. ion beam milling), to somewhat isotropic low energy plasma techniques that direct a plasma stream containing chemically reactive ions against a wafer to induce formation of volatile reaction products.

Intermediate between high energy sputtering techniques and low energy plasma techniques is a particularly useful dry etch process known as reactive ion etching. Reactive ion etching involves directing an ion containing plasma stream against a semiconductor, or other, wafer for simultaneous sputtering and plasma etching. Reactive ion etching retains some of the advantages of anisotropy associated with sputtering, while still providing reactive plasma ions for formation of vapor phase reaction products in response to contacting the reactive plasma ions with the wafer. In practice, the rate of wafer material removal is greatly enhanced relative to either sputtering techniques or low energy plasma techniques taken alone. Reactive ion etching therefore has the potential to be a superior etching process for construction of microdevices, with relatively high anistropic etching rates being sustainable. The micromachining techniques described above, as well as many others, are well known to those of skill in the art (see, e.g., Choudhury (1997) *The Handbook of Microlithography, Micromachining, and Microfabrication*, Soc. Photo-Optical Instru. Engineer, Bard & Faulkner (1997) *Fundamentals of Microfabrication*). In addition, examples of the use of micromachining techniques on silicon or borosilicate glass chips can be found in U.S. Pat. Nos. 5,194,133, 5,132,012, 4,908,112, and 4,891,120.

In one embodiment, the channel is micromachined in a silicon (100) wafer using standard photolithography techniques to pattern the channels and connection ports. Ethylene-diamine, pyrocatechol (EDP) is used for a two-step etch and a Pyrex 7740 coverplate can be anodically bonded to the face of the silicon to provide a closed liquid system. In this instance, liquid connections can be made on the backside of the silicon.

As indicated above, in a preferred embodiment, the channel is fabricated from a glass, quartz, or other capillary tube, such as a capillary electrophoresis tube.

B) Binding Partners

In a preferred embodiment, the channel(s) utilized in this invention bear, affixed to one or more surfaces one or more biological "binding partner(s)." A biological "binding partner" or a member of a "binding pair" refers to a molecule or composition that specifically binds other molecules to form a binding complex such as antibody-antigen, lectin-carbohydrate, nucleic acid-nucleic acid, biotin-avidin, etc.

The term "specifically binds", as used herein, when referring to a biomolecule (e.g., protein, nucleic acid, antibody, etc.), refers to a binding reaction which is determinative of the presence biomolecule heterogeneous population of proteins and other biologics. Thus, under designated conditions (e.g. immunoassay conditions in the case of an antibody, or stringent hybridization conditions in the case of a nucleic acid), the specified ligand or antibody binds to its particular "target" (e.g. a protein or nucleic acid) and does not bind in a significant amount to other molecules.

The binding partner(s) used in this invention are selected based upon the targets that are to be identified/quantified. Thus, for example, where the target is a nucleic acid the binding partner is preferably a nucleic acid or a nucleic acid binding protein. Where the target is a protein, the binding partner is preferably a receptor, a ligand, or an antibody that specifically binds that protein. Where the target is a sugar or glycoprotein, the binding partner is preferably a lectin, and so forth.

Suitable binding partners (capture agents) include, but are not limited to nucleic acids, proteins, receptor binding proteins, nucleic acid binding proteins, lectins, sugars, glycoproteins, antibodies, lipids, and the like. Methods of synthesizing or isolating such binding partners are well known to those of skill in the art.

1) Preparation of Binding Partners (Capture Agents)

a) Nucleic Acids

Nucleic acids for use as binding partners in this invention can be produced or isolated according to any of a number of methods well known to those of skill in the art. In one embodiment, the nucleic acid can be an isolated naturally occurring nucleic acid (e.g., genomic DNA, cDNA, mRNA, etc.). Methods of isolating naturally occurring nucleic acids are well known to those of skill in the art (see, e.g., Sambrook et al. (1989) *Molecular Cloning—A Laboratory Manual* (2nd Ed.), Vol. 1–3, Cold Spring Harbor Laboratory, Cold Spring Harbor, N.Y.).

However, in a preferred embodiment, the nucleic acid is created de novo, e.g. through chemical synthesis. In a preferred embodiment, nucleic acids (e.g., oligonucleotides) are chemically synthesized according to the solid phase phosphoramidite triester method described by Beaucage and Caruthers (1981), *Tetrahedron Letts.,* 22(20): 1859–1862, e.g., using an automated synthesizer, as described in Needham-VanDevanter et al. (1984) *Nucleic Acids Res.,* 12: 6159–6168. Purification of oligonucleotides, where necessary, is typically performed by either native acrylamide gel electrophoresis or by anion-exchange HPLC as described in Pearson and Regnier (1983) *J. Chrom.* 255: 137–149. The sequence of the synthetic oligonucleotides can be verified using the chemical degradation method of Maxam and Gilbert (1980) in Grossman and Moldave (eds.) Academic Press, New York, *Meth. Enzymol.* 65: 499–560.

b) Antibodies/Antibody Fragments

Antibodies or antibody fragments for use as binding partners (capture agents) can be produces by a number of methods well known to those of skill in the art (see, e.g., Harlow & Lane (1988) *Antibodies: A Laboratory Manual,* Cold Spring Harbor Laboratory, and Asai (1993) *Methods in Cell Biology Vol.* 37: *Antibodies in Cell Biology,* Academic Press, Inc. N.Y.). In one approach, the antibodies are produced by immunizing an animal (e.g. a rabbit) with an immunogen containing the epitope it is desired to recognize/capture. A number of immunogens may be used to produce specifically reactive antibodies. Recombinant protein is the preferred immunogen for the production of monoclonal or polyclonal antibodies. Naturally occurring protein may also be used either in pure or impure form. Synthetic peptides made as well using standard peptide synthesis chemistry (see, e.g., Barany and Merrifield, *Solid-Phase Peptide Synthesis;* pp. 3–284 in *The Peptides: Analysis, Synthesis, Biology. Vol. 2: Special Methods in Peptide Synthesis, Part A.,* Merrifield et al. (1963) *J. Am. Chem. Soc.,* 85: 2149–2156, and Stewart et al. (1984) *Solid Phase Peptide Synthesis,* 2nd ed. Pierce Chem. Co., Rockford, Ill.)

Methods of production of polyclonal antibodies are known to those of skill in the art. In brief, an immunogen, preferably a purified cytoskeletal component, is mixed with an adjuvant and animals are immunized. The animal's immune response to the immunogen preparation is monitored by taking test bleeds and determining the titer of reactivity to the cytoskeletal components and test compositions. When appropriately high titers of antibody to the immunogen are obtained, blood is collected from the animal and antisera are prepared. Further fractionation of the antisera to enrich for antibodies reactive to the cytoskeletal component can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein (1976) *Eur. J. Immunol.* 6: 511–519). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al. (1989) *Science,* 246:1275–1281.

Antibodies fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment from a library of greater than $10^{10}$ nonbinding clones. To express antibody fragments on the surface of phage (phage display), an antibody fragment gene is inserted into the gene encoding a phage surface protein (pIII) and the antibody fragment-pIII fusion protein is displayed on the phage surface (McCafferty et al. (1990) *Nature,* 348: 552–554; Hoogenboom et al. (1991) *Nucleic Acids Res.* 19: 4133–4137).

Since the antibody fragments on the surface of the phage are functional, phage bearing antigen binding antibody fragments can be separated from non-binding phage by antigen affinity chromatography (McCafferty et al. (1990) *Nature,* 348: 552–554). Depending on the affinity of the antibody fragment, enrichment factors of 20 fold–1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) *Nature,* 348: 552–554). Thus even when enrichments are low (Marks et al. (1991) *J. Mol. Biol.* 222: 581–597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) *J. Mol. Biol.* 222: 581–597). In one embodiment natural $V_H$ and $V_L$ repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) *J. Mol. Biol.* 222: 581–597; Marks et al. (1993). *Bio/Technology.* 10: 779–783; Griffiths et al. (1993) *EMBO J.* 12: 725–734; Clackson et al. (1991) *Nature.* 352: 624–628). Antibodies have been produced against self proteins, including human thyroglobulin, immunoglobulin, tumor necrosis factor and CEA (Griffiths et al. (1993) *EMBO J.* 12: 725–734). It is also possible to isolate antibodies against cell surface antigens by selecting directly on intact cells. The antibody fragments are highly specific for the antigen used for selection and have affinities in the 1 μM to 100 nM range (Marks et al. (1991) *J. Mol. Biol.* 222: 581–597; Griffiths et al. (1993) *EMBO J.* 12: 725–734). Larger phage antibody libraries result in the isolation of more antibodies of higher binding affinity to a greater proportion of antigens.

c) Binding Proteins

In one embodiment, the binding partner (capture agent) can be a binding protein. Suitable binding proteins include, but are not limited to receptors (e.g. cell surface receptors), receptor ligands, cytokines, transcription factors and other nucleic acid binding proteins, growth factors, etc.

The protein can be isolated from natural sources, mutagenized from isolated proteins or synthesized de novo.

Means of isolating naturally occurring proteins are well known to those of skill in the art. Such methods include but are not limited to well known protein purification methods including ammonium sulfate precipitation, affinity columns, column chromatography, gel electrophoresis and the like (see, generally, R. Scopes, (1982) *Protein Purification*, Springer-Verlag, N.Y.; Deutscher (1990) *Methods in Enzymology Vol. 182: Guide to Protein Purification*, Academic Press, Inc. N.Y.).

Where the protein binds a target reversibly, affinity columns bearing the target can be used to affinity purify the protein. Alternatively the protein can be recombinantly expressed with a HIS-Tag and purified using Ni2+/NTA chromatography.

In another embodiment, the protein can be chemically synthesized using standard chemical peptide synthesis techniques. Where the desired subsequences are relatively short the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond. This is typically accomplished using the same chemistry (e.g., Fmoc, Tboc) used to couple single amino acids in commercial peptide synthesizers.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield (1962) *Solid-Phase Peptide Synthesis*; pp. 3–284 in *The Peptides: Analysis, Synthesis, Biology. Vol. 2: Special Methods in Peptide Synthesis, Part A.*, Merrifield et al. (1963) *J. Am. Chem. Soc.*, 85: 2149–2156, and Stewart et al. (1984) *Solid Phase Peptide Synthesis*, 2nd ed. Pierce Chem. Co., Rockford, Ill.

In a preferred embodiment, the can also be synthesized using recombinant DNA methodology. Generally this involves creating a DNA sequence that encodes the binding protein, placing the DNA in an expression cassette under the control of a particular promoter, expressing the protein in a host, isolating the expressed protein and, if required, renaturing the protein.

DNA encoding binding proteins or subsequences of this invention can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066.

The nucleic acid sequences encoding the desired binding protein(s) may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant binding proteins can be purified according to standard procedures of the art as described above.

d) Sugars and Carbohydrates

Other binding partners include sugars and carbohydrates. Sugars and carbohydrates can be isolated from natural sources, enzymatically synthesized or chemically synthesized. A route to production of specific oligosaccharide structures is through the use of the enzymes which make them in vivo; the glycosyltransferases. Such enzymes can be used as regio- and stereoselective catalysts for the in vitro synthesis of oligosaccharides (Ichikawa et al. (1992) *Anal. Biochem.* 202: 215–238). Sialyltransferase can be used in combination with additional glycosyltransferases. For example, one can use a combination of sialyltransferase and galactosyltransferases. A number of methods of using glycosyltransferases to synthesize desired oligosaccharide structures are known. Exemplary methods are described, for instance, WO 96/32491, Ito et al. (1993) *Pure Appl. Chem.* 65:753, and U.S. Pat. Nos. 5,352,670, 5,374,541, and 5,545,553. The enzymes and substrates can be combined in an initial reaction mixture, or alternatively, the enzymes and reagents for a second glycosyltransferase cycle can be added to the reaction medium once the first glycosyltransferase cycle has neared completion. By conducting two glycosyltransferase cycles in sequence in a single vessel, overall yields are improved over procedures in which an intermediate species is isolated.

Methods of chemical synthesis are described by Zhang et al. (1999) *J. Am. Chem. Soc.*, 121(4): 734–753. Briefly, in this approach, a set of sugar-based building blocks is created with each block preloaded with different protecting groups. The building blocks are ranked by reactivity of each protecting group. A computer program then determines exactly which building blocks must be added to the reaction so that the sequences of reactions from fastest to slowest produces the desired compound.

2) Attachment of Binding Partners to the Channel

Many methods for immobilizing biomolecules to a variety of solid surfaces are known in the art. The desired component may be covalently bound, or noncovalently attached through specific or nonspecific bonding.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, Ichiro Chibata (1978) *Immobilized Enzymes*, Halsted Press, New York, and Cuatrecasas, (1970) *J. Biol. Chem.* 245: 3059.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

Where the binding partner is a nucleic acid or a polypeptide, the molecule can be chemically synthesized in situ. This involves essentially standard chemical synthesis methods substituting photo-labile protecting groups for the usual protecting groups (e.g. dimethoxy trityl group (DMT) used in nucleic acid synthesis). Irradiation of the microchannel at discrete locations results in selective coupling of the monomer (e.g. amino acid or nucleotide) to the growing polypeptide(s) or nucleic acid(s) at the irradiated site. Methods of light-directed polymer synthesis are well known to those of skill in the art (see, e.g., U.S. Pat. No. 5,143,854; PCT Publication Nos. WO 90/15070, WO 92/10092 and WO 93/09668; and Fodor et al. (1991) *Science,* 251, 767–77).

In preferred embodiments, the binding partner is immobilized by the use of a linker (e.g. a homo- or heterobifunctional linker). Linkers suitable for joining biological binding partners are well known to those of skill in the art. For example, a protein or nucleic acid molecule may be linked by any of a variety of linkers including, but not limited to a peptide linker, a straight or branched chain carbon chain linker, or by a heterocyclic carbon linker. Heterobifunctional cross linking reagents such as active esters of N-ethylmaleimide have been widely used (see, for example, Lerner et al. (1981) *Proc. Nat. Acad. Sci.* USA, 78: 3403–3407 and Kitagawa et al. (1976) *J. Biochem.,* 79: 233–236, and Birch and Lennox (1995) *Chapter 4 in Monoclonal Antibodies: Principles and Applications,* Wiley-Liss, N.Y.).

In one preferred embodiment, the binding partner is immobilized utilizing a biotin/avidin interaction. In this embodiment, biotin or avidin with a photolabile protecting group can be placed in the channel. Irradiation of the channel at a distinct location results in coupling of the biotin or avidin to the channel at that location. Then, the binding agent bearing a respective biotin or avidin is placed into the channel whereby it couples to the respective binding partner and is localized in the irradiated site. The process can be repeated at each distinct location it is desired to attach a binding partner.

Another suitable photochemical binding approach is described by Sigrist et al. (1992) *Bio/Technology,* 10: 1026–1028. In this approach, interaction of ligands with organic or inorganic surfaces is mediated by photoactivatable polymers with carbene generating trifluoromethyl-aryl-diazirines that serve as linker molecules. Light activation of aryl-diazirino functions at 350 nm yields highly reactive carbenes and covalent coupling is achieved by simultaneous carbene insertion into both the ligand and the inert surface. Thus, reactive functional groups are not required on either the ligand or supporting material.

In a most preferred embodiment, fused silica capillaries (50 $\mu$m i.d. are coated with a thin layer of epoxy (Epotek 350) in order to cover the fused silica surface with an organic coating. The organic coating of the surface not only minimizes DNA adsorption on the walls of the capillary, but also provides a polymerized surface to which DNA-probes can be immobilized directly. A protocol for coating the capillary surface with the epoxy is described by Liu et al. (1996) *J. Chromatogr.* 723: 157–167. Briefly, the capillary was rinsed first with acetone for 15 min., then dried in an oven at 100° C. for 1 h under a nitrogen pressure of 20 psi. Epoxy 314 ND (Epo-Tek, Billerica, Mass.) was dynamically coated onto the capillary surface by aspirating a solution of an epoxy mixture in acetone. The residual solvent was removed from the epoxy-coated capillaries by flushing with nitrogen at room temperature for 30 min. The epoxy coating is cross-linked at 80° C. for 30 min, then at 150° C. for 2 h under a nitrogen pressure of 20 psi. The coated capillaries are washed with buffer for 30 min prior to use.

A 1 cm section of the epoxy-coated capillary is then flushed with a specific DNA-probe solution. The DNA-probe solution is allowed to react with the capillary piece overnight to bind the DNA-probe to the capillary walls via hydrophobic and electrostatic interactions. Other DNA-probes are attached to similar one cm long pieces of coated capillaries in a similar manner. Once the are immobilized onto the capillary walls, these hybridization regions are rinsed with deionized water, and are then ready to assemble into a capillary biosensor having different binding partners at different locations.

C) Analyte Detection Methods

Virtually any method of biological molecule detection can be used in accordance with the methods of this invention. Since the identity of the various analytes is determined by their spatial position in the flow moving through the channel, there is not need for different labeling systems on each analyte. To the contrary, one advantage of the present assay system is that there is no need to label the analyte at all.

Methods of detecting analytes are well known to those of skill in the art. Were the analyte is labeled (e.g. with a radioactive, fluorescent, magnetic, or mass label), the analyte is detected by detecting the label. However, in a preferred embodiment, the analyte is not labeled and preferred detection methods do not rely on the use of labels attached to the analyte. Such detection means include, but are not limited to detection of optical signals (e.g. emission and/or absorption spectroscopy), detection of electrical and magnetic signals, detection of changes of the electrical properties (e.g. conductance/resistance, capacitance, impedance, etc.) of the medium containing the analyte.

In one simple embodiment, the optical absorption of the fluid containing the analyte is monitored (e.g. with a standard ultra-violet) detector. However, in a preferred embodiment, an electroanalytic detector is utilized. In a most preferred embodiment, the electroanalytic detector utilizes sinusoidal voltammetry.

In a particularly preferred embodiment, sinusoidal voltammetry involves providing a small amount of the analyte of interest to a voltammetric electrode. A sinusoidal (or other time-varying) voltage is applied to the electrode. The sinusoidal voltage has an amplitude large enough to sweep through the formal potential of the redox species of interest in a single cycle at a given frequency. The response of the analyte to the sinusoidal voltage is selectively detected at a harmonic of the fundamental frequency of the sinusoidal voltage. Methods of performing sinusoidal voltammetry are provided in U.S. Pat. No. 5,650,061 and the references cited therein.

It was a discovery of this invention that combination of sinusoidal voltammetry detection with spatially encoded analyte separation provides highly specific analyte detection/quantitation at extremely low levels in a complex sample (e.g. serum).

III. Integrated Assay Device

State-of-the-art chemical analysis systems for use in chemical production, environmental analysis, medical diagnostics and basic laboratory analysis are preferably capable of complete automation. Such total analysis systems (TAS) (Fillipini et al. (1991) *J. Biotechnol.* 18: 153; Garn et al (1989) *Biotechnol. Bioeng.* 34: 423; Tshulena (1988) *Phys. Scr.* T23: 293; Edmonds (1985) *Trends Anal. Chem.* 4: 220; Stinshoff et al. (1985) *Anal. Chem.* 57:114R; Guibault (1983) *Anal. Chem Symp. Ser.* 17: 637; Widmer (1983) *Trends Anal. Chem.* 2: 8) automatically perform functions ranging from introduction of sample into the system, transport of the sample through the system, sample preparation, separation, purification and detection, including data acquisition and evaluation.

Recently, sample preparation technologies have been successfully reduced to miniaturized formats. Thus, for example, gas chromatography (Widmer et al. (1984) *Int. J. Environ. Anal. Chem.* 18: 1), high pressure liquid chromatography (Muller et al. (1991) *J. High Resolut. Chromatogr.* 14: 174; Manz et al.. (1990) *Sensors & Actuators* B1:249; Novotny et al., eds. (1985) *Microcolumn Separations: Columns, Instrumentation and Ancillary Techniques J. Chromatogr. Library*, Vol. 30; Kucera, ed. (1984) *Micro-Column High Performance Liquid Chromatography*, Elsevier, Amsterdam; Scott, ed. (1984) *Small Bore Liquid Chromatography Columns: Their Properties and Uses*, Wiley, N.Y.; Jorgenson et al. (1983) *J. Chromatogr.* 255: 335; Knox et al. (1979) *J. Chromatogr.* 186:405; Tsuda et al. (1978) *Anal. Chem.* 50: 632) and capillary electrophoresis (Manz et al. (1992) *J. Chromatogr.* 593: 253; Olefirowicz et al. (1990) *Anal. Chem.* 62: 1872; *Second Int'l Symp. High-Perf. Capillary Electrophoresis* (1990) *J. Chromatogr.* 516; Ghowsi et al. (1990) *Anal. Chem.* 62:2714) have been reduced to miniaturized formats.

Similarly, in another embodiment, this invention provides an integrated assay device (e.g., a TAS) for detecting and/or quantifying a multiplicity of analytes. The assay device comprises the channel(s) with attached binding partners as described above. In addition, preferred integrated assay devices also include one or more of the following: a detection system (e.g. voltammetry system including electrodes and/or associated electronics), one or more reservoirs to provide buffers and/or flushing fluids, sample application well(s) and/or injection port(s), a computer controller (for control of pumps, reservoir flow switching, detector, and signal analysis system, and the like.

In a particularly preferred embodiment, the integrated assay device contains the channels in a "removable" unit. Thus, for example, where the capillaries can be provided as channels in a module that can be easily inserted and removed from the ancillary equipment thereby readily allowing the device to be run with assay for different sets of analytes.

Where the channel used in the device is a tube (e.g. a capillary electrophoresis tube), a conventional capillary electrophoresis device contains much of the ancillary plumbing, sample handling and delivery components, and computer controller(s) for an "integrated" assay device according to the present invention. Little more is required than fairly straightforward introduction/addition of a detector (e.g. a sinusoidal voltammetry detector) and associated electronics in accordance with this invention to provide an integrated assay device well suited to detection and/or quantitation of a wide variety of analytes.

IV. Running Assays

In general, assays are run by introducing the sample into the channel having affixed binding partners. The sample is preferably held under conditions that allow the binding partner to specifically bind the target analytes that may be present in the sample. The sample is then flushed out of the channel, typically by introduction of a buffer that facilitates release of the bound analyte. The analyte is then detected at a downstream detection point and the identity of the analyte is determined by the time from release to detection.

A) Sample Preparation

Virtually any sample can be analyzed using the devices and methods of this advantage. However, in a preferred embodiment, the sample is a biological sample. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, cerebrospinal fluid, blood, blood fractions (e.g. serum, plasma), blood cells (e.g., white cells), tissue or fine needle biopsy samples, urine, peritoneal fluid, and pleural fluid, or cells therefrom. Biological samples may also include sections of tissues such as frozen sections taken for histological purposes.

Biological samples, (e.g. serum) may be analyzed directly or they may be subject to some preparation prior to use in the assays of this invention. Such preparation can include, but is not limited to, suspension/dilution of the sample in water or an appropriate buffer or removal of cellular debris, e.g. by centrifugation, or selection of particular fractions of the sample before analysis.

B) Sample Delivery Into System

The sample can be introduced into the devices of this invention according to standard methods well known to those of skill in the art. Thus, for example, the sample can be introduced into the channel through an injection port such as those used in high pressure liquid chromatography systems. In another embodiment the sample can be applied to a sample well that communicates to the channel. In still another embodiment the sample can be pumped into the channel. Means of introducing samples into channels are well known and standard in the capillary electrophoresis and chromatography arts.

C) Binding Conditions

Once in the channel, the sample is held under conditions that promote specific binding between the sample and the binding partner. Conditions compatible with specific binding between a binding partner and an analyte are well known to those of skill in the art. For example, buffers suitable for promoting binding between an antibody and a target protein are well known in the immunoassay art (see, e.g., U.S. Pat. Nos. 4,366,241; 4,376,110; 4,517,288; and 4,837,168, Asai (1993) *Methods in Cell Biology Volume* 37: *Antibodies in Cell Biology*, Academic Press, Inc. New York; Stites & Terr (1991) *Basic and Clinical Immunology* 7th Edition). Similarly conditions under which a nucleic acids specifically hybridize to each other are also well know to those of skill in the art (see, Tijssen (1993) supra.). The particular binding conditions are optimized for particular sets of binding partners and target analytes according to standard methods well known to those of skill in the art (see, e.g., Tijssen (1993) supra., U.S. Pat. Nos. 4,366,241; 4,376,110; 4,517,288; and 4,837,168, Asai (1993) *Methods in Cell Biology Volume* 37: *Antibodies in Cell Biology*, Academic Press, Inc. New York; Stites & Terr (1991) *Basic and Clinical Immunology* 7th Edition).

D) Release Conditions

After the analyte(s) in the sample are specifically bound to the binding partner attached to the channel, they are released. Release is preferably accomplished by contacting the binding partner/analyte complex with a buffer or with temperature conditions that disrupt the binding partner/analyte interaction. Depending on the particular analyte/binding partner pair such associations can be disrupted by the use of high temperature, denaturants (e.g. urea, formamide, etc.), high or low pH, high or low salt, and various chaotropic agents (e.g., guanidine HCl).

E) Analyte/Flow Through the Channel

Samples and/or carrier/buffer fluids can be introduced into and/or moved through the channel according to standard methods. For example, fluid can be introduced and moved through the cannel by a simple gravity feed from a "reservoir". Alternatively, fluids can be moved through the channel by gas pressure, or by fluid pressure produced by any of a variety of suitable pumps (e.g. peristaltic pumps, metering pumps, etc.), pressure on a deformable chamber/diaphragm, etc.. Analytes can also be driven through the channel by electroosmotic methods.

F) Detection

As indicated above, analyte detection can be by any of a number of methods well known to those of skill in the art as indicated above. In a preferred embodiment, electrochemical detection methods are utilized and in a most preferred embodiment, detection is by sinusoidal voltammetry.

The protocol for performing sinusoidal voltammetry has been described previously (Singhal et al. (1997) *Anal. Chem.* 69: 4828–4832; and U.S. Pat. No. 5,650,061). Briefly, a sine wave at 2 Hz, 0.7 Vp-p, +0.35 V D.C. offset is generated digitally using a software program. This sine wave serves as the applied potential for a copper electrode. The current response from the electrode is collected by the software in real time for the entire length of a single elution run. This time domain current response is then converted into the frequency domain with fast Fourier transforms. The protocol for analyzing frequency spectra has been explained previously (Singhal et al. (1997) *Anal. Chem.* 69: 1662–1668). The spectrum corresponding to the analyte is obtained after background subtraction and digital phase locking as described previously (Singhal et al. (1997) supra.).

V. Kits for Multiple Analyte Detection

In one embodiment this invention provides kits for screening for identifying the presence or absence, or quantifying a multiplicity of analytes in a sample. The kits include of the channels of this invention bearing affixed to their surfaces various binding partners as described herein. The channels can be designed for simple and rapid incorporation into an integrated assay device, e.g. a device comprising electrochemical detector (e.g. sinusoidal voltammetry) circuitry, appropriate plumbing for administration of a sample and maintenance of a fluid flow through the channel, and computer control system(s) for control of sample application, fluid flow, and analysis of signal output as described herein. The kit can additionally include appropriate buffers and other solutions and standards for use in the assay methods described herein.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Nanoliter Volume Electrochemical Sensing of DNA-Hybridization

Materials and Methods

Reagents

The water used was deionized and then passed through a Milli-Q Water Purification System (Millipore Corp., Bedford, Mass.). The biotinylated DNA-probe and the complementary DNA-target specific to Tuberculosis (TB) and Human Immunodeficiency Virus (HIV) identification were custom synthesized through Genemed Synthesis, Inc., San Francisco, Calif. (Table 1). DNA-probe solutions were made by diluting a 100 $\mu$g/ml solution of DNA-probe dissolved in deionized water into a 1:1 mixture with DNA-binding solution (Pierce Chemicals, CA). This binding solution facilitates binding DNA to polymerized surfaces via hydrophobic and electrostatic interactions. Fused silica capillaries (Polymicron Technologies, Inc., AZ) were used for making the capillary biosensors. These capillaries were not flushed with acetone and dried before any derivatization was done to the capillary surface.

Capillary Derivatization and Immobilization of DNA-probes

Fused silica capillaries (50 $\mu$m i.d.×150 $\mu$m o.d., one meter in length) were used for the biosensor. The capillary was coated with a thin layer of epoxy (Epotek 350) in order to cover the fused silica surface with an organic coating. Organic coating of the surface not only minimizes DNA adsorption on the walls of the capillary, but also provides a polymerized surface to which DNA-probes can be immobilized directly. The protocol for coating the capillary surface with the epoxy was exactly as described by Liu et al. (1996) *J. Chromatogr.* 723: 157–167. Briefly, the capillary was rinsed first with acetone for 15 min., then dried in an oven at 100° C. for 1 h under a nitrogen pressure of 20 psi. Epoxy 314 ND (Epo-Tek, Billerica, Mass.) was dynamically coated onto the capillary surface by aspirating a solution of an epoxy mixture in acetone. The residual solvent was removed from the epoxy-coated capillaries by flushing with nitrogen at room temperature for 30 min. The epoxy coating was cross-linked at 80° C. for 30 min, then at 150° C. for 2 h under a nitrogen pressure of 20 psi. The coated capillaries were washed with buffer for 30 min prior to use.

A 1 cm section of the epoxy-coated capillary was then flushed with a specific NA-probe solution. The DNA-probe solution was allowed to react with the capillary piece overnight to bind the DNA-probe to the capillary walls via hydrophobic and electrostatic interactions. Other DNA-probes was attached to similar one cm long pieces of coated capillaries in a similar manner. Once the probes were immobilized onto the capillary walls, these hybridization regions were rinsed with deionized water, and then were ready to assemble into the capillary biosensor. These hybridization regions were epoxied into a "separation column" at two different locations, where the distance from the inlet to the first probe (TB probe) was about 25 cm, and the two probes were spaced 15 cm apart. This left a distance of approximately 60 cm from the second probe (HIV probe) to the detector. The different segments of capillary were linked together by epoxying the capillaries into sleeves (180×360 μm capillary sections) which were also approximately one cm in length each. The total length of the capillary biosensor was approximately one meter.

Hybridization, Elution and Detection of DNA-Target

The capillary was mounted in a commercial capillary electrophoresis instrument (Biorad Instruments Inc, Hercules, Calif.), which was used for its pressure flow and autosampler capabilities. The protocols used for hybridizing complementary targets to these DNA-probes with high stringency have been described extensively in the literature. The specific procedures used for this experiment are as follows:

The capillary was initially flushed with prehybridization buffer (0.75 M NaCl, 75 mM sodium citrate, pH=7.0, 0.1% N-lactoyl sarcosine, 0.02% SDS, in 50% formamide, 40° C.) in order to selectively bind complementary DNA-targets to the probe. DNA-target solutions for both TB and HIV targets were dissolved in Prehybridization Buffer, and flushed and incubated in the capillary for nearly 30 minutes in order to achieve complete hybridization and saturation of the surface immobilized probes.

The excess target solution was then rinsed out with Hybridization Buffer (0.3 M NaCl, 30 mM sodium citrate, pH=7.0, 0.1% SDS). A stringent wash was subsequently done with Stringent Wash Buffer (75 mM NaCl, 7.5 mM sodium citrate, pH=7.0, 0.1% SDS, at 40° C.) in order to remove any non-specifically bound DNA-targets). This stringent wash ensured that only perfectly complementary DNA-targets remained behind inside the capillary biosensor, as everything else is washed out under these stringent conditions.

The capillary was then filled up with Electrochemical Wash Buffer (89 mM TRIS, 89 mM boric acid, and 1 mM EDTA, pH=10), in order to rinse out the high stringency wash buffer which was not compatible with the copper electrode (due to the presence of surfactants).

Once the capillary was filled with Electrochemical Wash Buffer, the copper electrode was placed at the biosensor capillary outlet. The electrode was automatically aligned with the capillary outlet due to a two-part machined design (Kuhr (1993) U.S. Pat. No. 5,650,061). The capillary was then filled rapidly (at 100 psi) with Elution Buffer (89 mM Tris, 89 mM boric acid, and 1 mM EDTA, pH=11), and incubated for 30 minutes at room temperature. The Elution Buffer promoted denaturation of the hybridized DNA-targets, thereby releasing the oligomers into solution inside the capillary at specific locations.

The Elution Buffer, containing the dehybridized target DNA was then pumped at a constant flow rate using pressure induced flow at nearly 5 psi, thereby eluting the released DNA-targets as they moved with the buffer. As the DNA-target oligomers flowed past the detector, the DNA was electrocatalytically oxidized at the copper electrode, and thereby generated a signal which could be detected using sinusoidal voltammetry as described previously (see U.S. Pat. No. 5,650,061). Each separate zone of DNA was then detected at the copper electrode at the outlet at it moves past the detector.

Electrochemical Detection

Forty-micron diameter copper microelectrodes were fabricated inside a 5 cm, 50×360 μm fused silica capillary. The capillary was filled with gallium using a syringe. Next, a small length of copper wire was inserted into the capillary at one end, and then sealed in place using 5-minute epoxy. Another wire was inserted in from the back end of the capillary to provide an electrical connection to the copper wire. The gallium inside the capillary provided an electrical connection between the two wires. These capillary microelectrodes were very rugged, and reusable after polishing. These electrodes were not pretreated in any form except for a manual polish using 600-grit sand paper.

Sinusoidal voltammetry was used to detect the dehybridized DNA target at the copper microelectrode as it eluted from the capillary. The protocol for performing sinusoidal voltammetry has been described previously (Singhal et al. (1997) Anal. Chem. 69: 4828–4832; and U.S. Pat. No. 5,650,061). Briefly, a sine wave at 2 Hz, 0.7 Vp-p, +0.35 V D.C. offset was generated digitally using a in-house software program. This sine wave served as the applied potential for the copper electrode. The current response from the electrode was collected by the software in real time for the entire length of a single elution run. This time domain current response was then converted into the frequency domain with fast Fourier transforms. The protocol for analyzing frequency spectra has been explained previously (Singhal et al. (1997) Anal. Chem. 69: 1662–1668). The spectrum corresponding to the analyte was obtained after background subtraction and digital phase locking as described previously (Singhal et al. (1997) supra.).

Results and Discussion

Low volume, direct detection of DNA hybridization is desirable due to the clinical importance of DNA as an indicator of disease. Once a specific nucleotide sequence has been shown to be uniquely or distinguishably associated with a given marker (e.g. an infectious agent, genetic trait, tumor type), that sequence can be synthesized in large quantity and used as a probe for nucleic acid from other sources to determine if the specific sequence is present. DNA assays based on hybridization have been developed for a number of different applications, and in many cases, multiple tests need to be performed on every sample to completely fingerprint and identify the DNA present.

Sinusoidal Voltammetry, a frequency domain voltammetric detection technique, can be used to detect nucleic acids under experimental conditions similar to those used for the detection of sugars. Since nucleotides also contain amine moieties on the nucleobases, and these are also electroactive at a copper surface, it was possible that some signal on the nucleotides could be contributed by these bases apart from that due to the sugar backbone.

Detection of underivatized DNA is highly desirable in order to avoid any sample handling losses and contamination problems. Electrochemical detection is particularly suited for the generally sample-limited case of DNA analysis, as it can be miniaturized with ease (capable of working in nanoliter to picoliter volumes) without sacrificing its capabilities as a sensitive detector.

In the development of this capillary biosensor, specific sequences of DNA have been immobilized in different regions inside a continuous microfluidic channel (i.e., a fused silica capillary). A 1-cm section of a 50 μm i.d. capillary, corresponding to a sample volume of 20 nL, was used to provide the recognition region of the sensor. The sample was pumped through each region sequentially, where the appropriate DNA targets (if present) could bind to each immobilized DNA probe independently. Once the sample had a chance to interact with each immobilized target, it was eluted from the capillary and the entire capillary was washed with a series of stringent washes, thereby removing any potential contaminating materials. The target DNA that remained bound to each region of immobilized probe was then eluted in a spatially encoded manner.

FIG. 1 shows the fundamental approach used in this design to enable the possibility of observing multiple hybridization events in a single experiment. Zones 1 and 2 are immobilization zones to which DNA-probes for TB and HIV were attached, respectively. These zones were subsequently combined to make a single capillary system, so as to use only one injection of a sample containing the DNA targets. The reagents needed to wash a more complex sample with very high stringency (i.e., a clinical sample which contains many other biomolecules like proteins, other cell lines etc.) can be introduced via pressure-induced flow from reservoirs at the head of the capillary. The copper microelectrode is poised at the outlet end of the capillary; it is positioned using a machined two-part system that allows automatic alignment of the capillary with the electrode (Kuhr et al. U.S. Pat. No. 5,650,061). Thus the system is very easy to put together, and robust once in operation.

Figure 2:
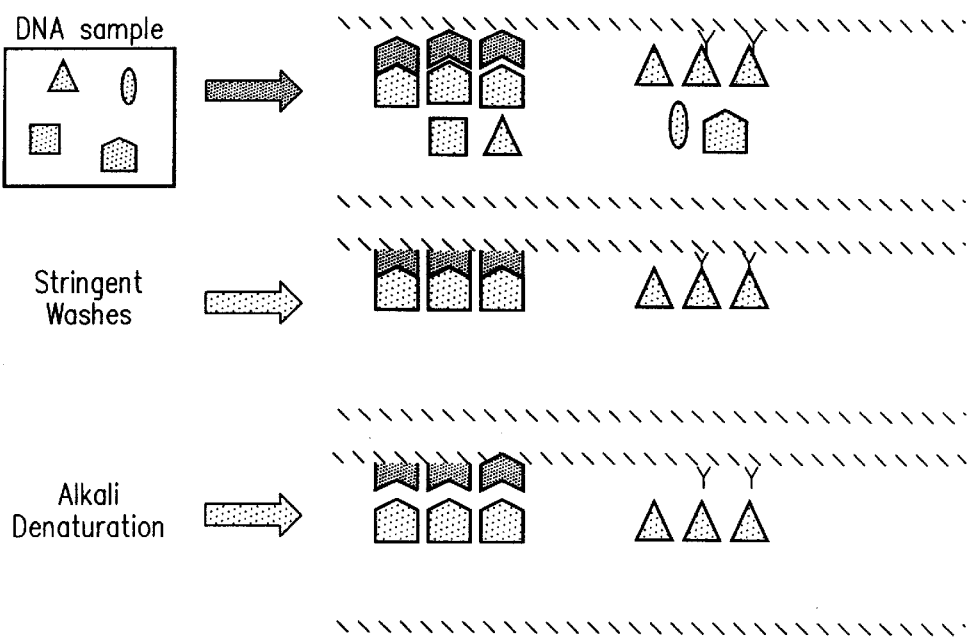
FIG. 2 shows protocols for performing stringent hybridization and alkali denaturation of DNA-targets inside the capillary biosensor. (1) Hybridize the various DNA-targets to the probes immobilized on the capillary surface. (2) Stringent washes are then performed to remove any non-specific adsorbed or hybridized DNA. (3) Finally, alkali denaturation is performed to elute the previously hybridized DNA-targets from the capillary biosensor.

The sequence of steps used to achieve specific hybridization, washing, and elution of the denatured targets oligonucleotides is shown in FIG. 2. Similar steps can be utilized for any kind of stringent hybridization of DNA-targets to their complementary probes. In this scheme:

1) Hybridization is carried out under stringent conditions to avoid any non-specific binding of the targets to the capillary walls or to probes that are not perfect complements to the target analyte. Consequently, the TB-target (the oligomer which has a sequence characteristic of DNA coding for TB, Zone 1) only hybridizes to the immobilized TB-probe (the complementary sequence), and the HIV-target only hybridizes to the immobilized HIV-probe (Zone 2) under stringent conditions. These zones are spatially segregated and stringent washes remove all interfering components form each zone, as well as from the capillary separating the zones.

2) The final wash with Elution Buffer (TBE, pH=11) denatures the hybridized complementary nucleic acids simultaneously, thereby releasing the bound DNA targets into the solution immediately adjacent to the immobilized probe(s) in the capillary. The spatial selectivity for these two targets is conserved since this buffer is rapidly moved into place (on a time scale much faster than dehybridization can take place), then flow within the capillary is halted, and the denaturation process is complete after 30 minutes of incubation.

Figure 3:
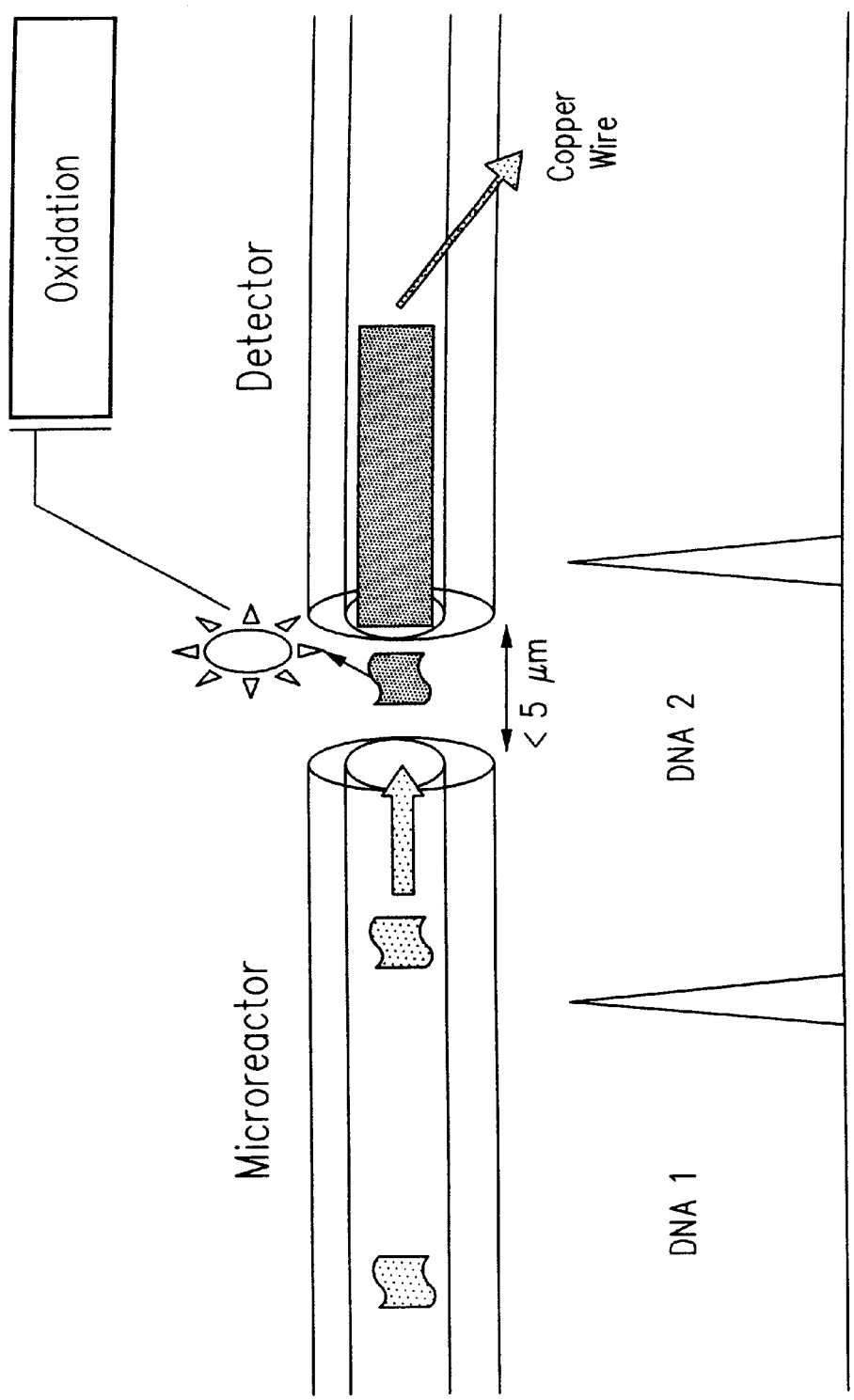
FIG. 3 provides a schematic of the elution of alkali denatured DNA-targets from a capillary biosensor, and consequent electrochemical detection. The electrode is fabricated inside a capillary piece with the same diameter as the biosensor capillary to facilitate auto-alignment. The electrode lies very close (<5 µm) to the outlet of the biosensor capillary. The lower trace shows a schematic of the detection of the DNA-targets as they elute from the biosensor capillary.

3) Finally, the solution containing the "free" spatially-resolved target-DNA oligomers was eluted. Since the zones containing the two targets are spatially distinct, they flow past the copper electrode poised at the outlet at different times. The scheme shown in FIG. 3 illustrates this aspect of detecting the eluting DNA-targets. The elution time of each target at the detector indicate its identity, thereby encoding the site of DNA-hybridization.

Figure 4:
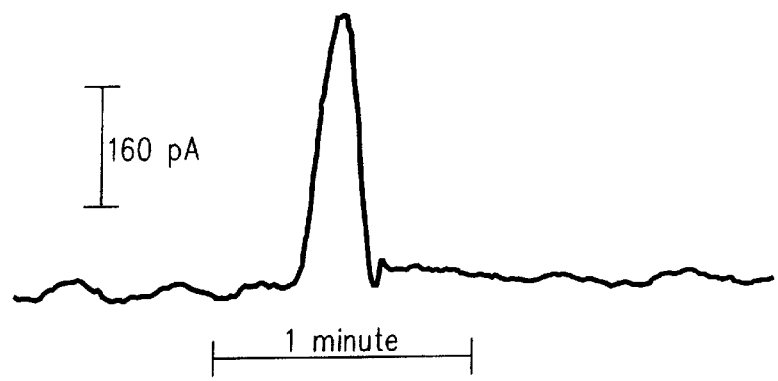
FIG. 4 illustrates detection of HIV-specific target using capillary biosensor and sinusoidal voltammetric detection. 10 µg/ml HIV-specific target flushed inside a capillary biosensor with HIV-specific probe immobilized only. All hybridization conditions as described herein. The sinusoidal voltammetric excitation waveform was 2 Hz, at 0–700 mVp-p. The signal shown was obtained at the $5^{th}$ harmonic.

The detection of HIV-target DNA using a capillary biosensor with a 1-cm zone of immobilized DNA-probe is shown in FIG. 4. A sample containing 100 $\mu$L of 10 $\mu$g/ml of a synthetic HIV-target was flushed through the capillary biosensor, where the HIV-probe was immobilized. The sequence of steps described in FIG. 2 was followed to allow the detection of HIV-oligonucleotide target in the sample. Originally, the sequence did not include the electrochemical wash buffer (89 mM TRIS, 89 mM boric acid, and 1 mM EDTA, pH=10). This was added to minimize the artifact observed when the Elution Buffer hits the copper electrode. The pH of this buffer is critical, since too high a pH will lead to dehybridization of the target DNA and result in loss of signal, while too low a pH will result in a large artifact when the Elution Buffer reaches the detector.

As shown in FIG. 4, the signal obtained with sinusoidal voltammetry demonstrates the elution of the DNA-target after dehybridization in Elution Buffer. The elution of a blank solution shows that the signal is very stable, but it is difficult to assess the specificity of binding of the HIV-target with a single probe system. Thus, this kind of detection could lead to false positives in DNA testing.

Figure 5:
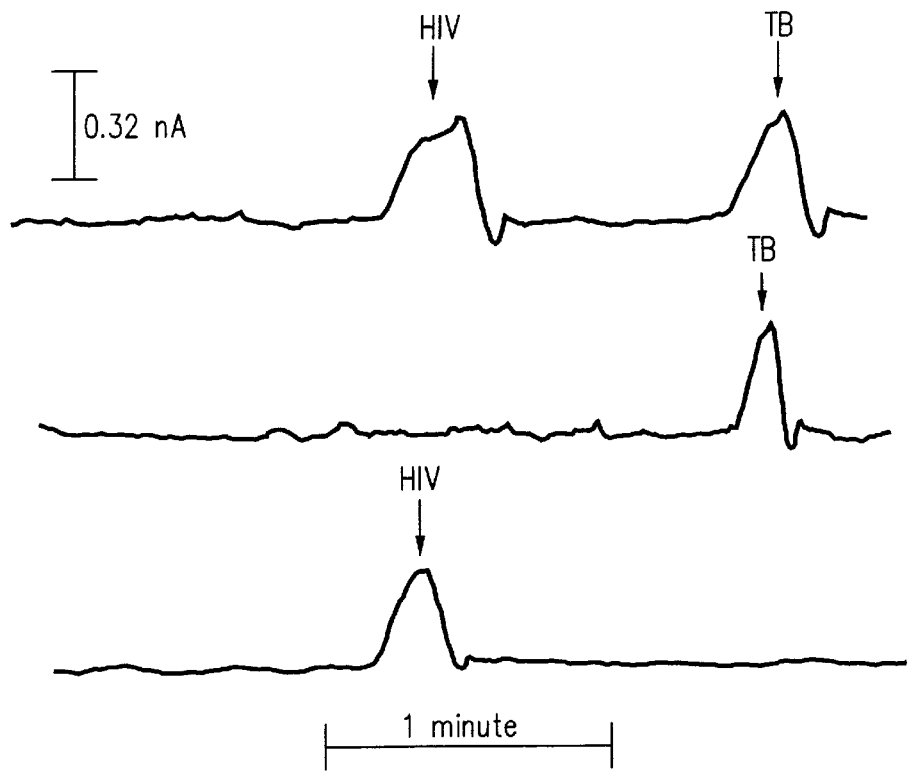
FIG. 5 shows the detection of multiple DNA-targets simultaneously using flow-encoded hybridization assay. Sample used contained a 1:1 mixture of HIV, and TB-specific targets, each at a concentration of 10 µg/ml. All hybridization and elution conditions same as in FIG. 4 and as described in experimental section. Signal shown was obtained at the $5^{th}$ harmonic, as it was found to have the best sensitivity for detection.

A multiple probe system can not only address the issues of parallel processing of nucleic acid samples, but also provides an internal standard against non-specific hybridization in its inherent design. If non-specific hybridization occurs in a given sample, it would give more than one peak in a multiple probe system. This would immediately indicate the need for an even more stringent hybridization protocols, until a single peak is detected for a single injected target. The specificity of hybridization for the current system is demonstrated in FIG. 5(A), with the detection of hybridization of TB and HIV-specific targets simultaneously present in the same sample. The sample was allowed to interact with each DNA-probe only once, but the two targets can be detected simultaneously in one run. The migration times for the two zones match with internal standards for TB and HIV targets shown in FIGS. 5(B) and 5(C) respectively. Thus, not only does this illustrate that the two targets can be detected simultaneously, but also that there was no non-specific hybridization occurring under the hybridization conditions being used. Otherwise, the internal standard runs would have shown not one, but two peaks (i.e., the TB-specific target would have hybridized to its perfect complement probe, and to the HIV-specific probe, and similarly for the HIV-specific target). Thus, the detection of two peaks in FIG. 5(A) definitely indicates the detection of synthetic TB and HIV-specific targets simultaneously and demonstrates the absence of non-specific hybridization, reducing the likelihood of the generation of any false positive results.

DNA sequencing by hybridization relies on the molecular recognition imparted via the hybridization of a sample (e.g. target) DNA molecule to an immobilized probe DNA. Preferred probe oligonucleotides are at least about 7 nucleotides in length more preferably at least about 10 nucleotides in length, more preferably at least 15 or 20 nucleotides in length and most preferably at least 30, 40 or 50 nucleotides in length. This probe has a known sequence that is complementary to at least one region of the target. While there are many different assay formats, the probe is typically immobilized to nitrocellulose, agarose, plastic or other inert substrate that can be placed in contact with the sample, washed clean of non-recognized DNA, then assayed for content. The assay of hybridized DNA can be accomplished in the system described here following denaturation of the DNA, elution from the capillary or channel and detection with SV at a copper microelectrode.

Conclusions

A new capillary-based DNA-biosensor has been developed utilizing direct electrochemical detection which is capable of detecting multiple DNA oligomers simultaneously. This detection scheme utilized the flow-encoded hybridization assay of DNA-targets in a sample with various DNA-probes immobilized at various positions on a capillary surface. The simultaneous hybridization of various types of DNA-targets is complemented by the direct detection of these targets once they are eluted, at a copper electrode by using sinusoidal voltammetry. Such parallel, and native detection of disease-specific oligonucleotide sequences can pave the way for a multi-disease DNA-sensor which is robust, rugged, and cheap. Thereby, it avoids the problems with existing DNA-sensors which are based on various optical detection schemes that are operator intensive and expensive to perform.

Example 2

Sensitive and Selective Detection of Amino Acids and Peptides with Sinusoidal Voltammetry Experimental Parameters Reagents The water used was deionized and then passed through a Milli-Q water purification system (Millipore Corp., Bedford, Mass.). The amino acids and Insulin (98–99%, Sigma Chemical Corp., St. Louis, Mo.), and the remaining peptides (Peninsula Laboratories, Inc., San Carlos, Calif.) were used as received. All experiments were done with 0.10 M sodium hydroxide (A.C.S. Grade, Fisher Scientific, Fair Lawn N.J.) as the running electrolyte. Stock solutions of 0.10 M were prepared in deionized water. Subsequent dilutions were made using the running electrolyte.

Copper Microelectrodes

Copper microelectrodes were prepared by first pulling glass capillaries with a microelectrode puller (Model PE-2, Narishige, Tokyo Japan). Then, under a microscope the end of the capillary was clipped with a scalpel. A 20 $\mu$m diameter copper wire (99.99%, Goodfellow, Cambridge, England) was then inserted into the freshly clipped end and sealed with epoxy (Epoxy Technology, Billerica, Mass.). The electrode was polished on a diamond-polishing wheel and cleaned by sonication in deionized water. To make electrical connection with the copper wire, the back end of the capillary was filled with gallium (Sigma Chemical Co.) and a 150 $\mu$m diameter copper wire inserted into the gallium. Alternatively, the back end of the capillary was filled with epoxy and the larger diameter copper wire was placed in the epoxy filled capillary until it physically made contact with the 20 $\mu$m wire. No electrochemical pretreatment was performed and the electrode was allowed to stabilize under experimental conditions for about an hour or until a stable response was observed.

Electrochemical Instrumentation and Experimental Conditions

The flow cell was constructed of Plexiglass and the tubing was matched so that diffusional broadening was avoided. The introduction of the sample plug was controlled via a pneumatic actuator, which is controlled by a solenoid valve. The flow rate was maintained by gravity flow by keeping the buffer reservoir 19 cm above the flow cell. The flow rate was determined to be 0.5 ml/min and the volume of the sample was determined from the flow rate and length of the injection. The injection time was determined so that the electrode saw the full concentration of the analyte.

The conditions for the experiments reported are described here. For the amino acids and peptides a 2 Hz sine wave (0 to 690 mV vs Ag/AgCl) was applied with software written by the author in Labview (National Instruments, Austin, Tex.). The waveform was filtered with a 4-pole low pass filter using a cyberamp (Model 380, Axon Instruments Inc., Foster City, Calif.) with a 3-db point of three times the fundamental frequency (6 Hz). The output current was filtered with a 4-pole low pass filter. The filter was set at 40 Hz (4 times the maximum frequency observed, $10^{th}$ harmonic or 20 Hz). The current was converted from digital to analog with a 16 bit analog to digital converter (PCI-4451, National Instruments) using a 300 MHz Pentium II personal computer. A single scan comprised 4 sinusoidal cycles.

The time domain collected was converted into the frequency domain by Labview software (National Instruments) and further processed by using Matlab programming (The Mathworks, Inc., Englewood Cliffs N.J.). The signal only spectra were obtained by subtracting the background vector obtained prior to injection from the instantaneous signal current vector. A digital lock-in amplification method was used to acquire the time domain spectra. The time spectra were Fourier transformed at a rate of 512 points to generate the magnitude and phase angle of each frequency harmonic (up to the $10^{th}$ harmonic). The phase information at each harmonic was obtained by using the signal only vector and projecting it onto the background-subtracted signal vector. Lastly, the phase resolved vectors were low-passed filtered using a moving average smooth (boxcar integration).

Results.

Figure 6:
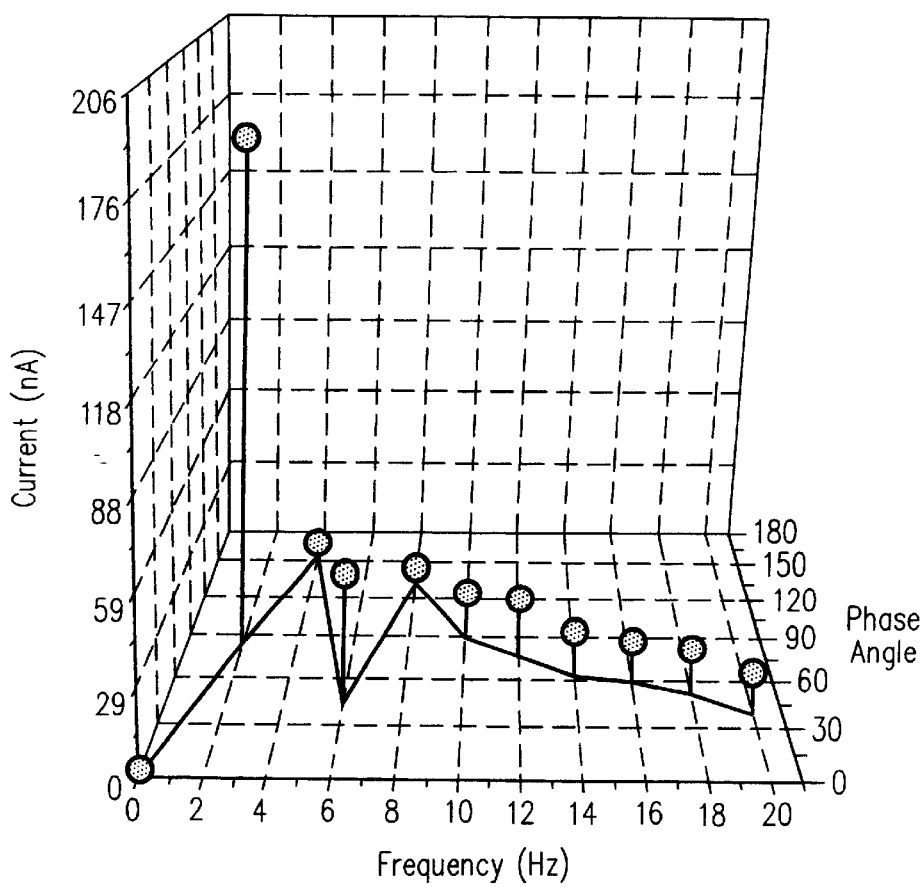
FIG. 6 shows the background subtracted frequency spectrum for Arginine at a copper microelectrode. The three dimensional graph consists of the frequency (x-axis), magnitude (z-axis) and phase angle (y-axis) information out to the $10^{th}$ harmonic.

FIG. 6 shows the background subtracted frequency spectrum for Arginine at a copper microelectrode. The experiment was performed using 1 $\mu$M Arginine. The excitation signal was a sine wave: 2 Hz, 0–690 mV vs. Ag/AgCl. Current from four sinusoidal periods which consisted of 512 points (total time=1 sec) was used to generate each frequency spectrum. The three dimensional graph consists of the frequency (x-axis), magnitude (z-axis) and phase angle (y-axis) information out to the $10^{th}$ harmonic.

Figure 7:
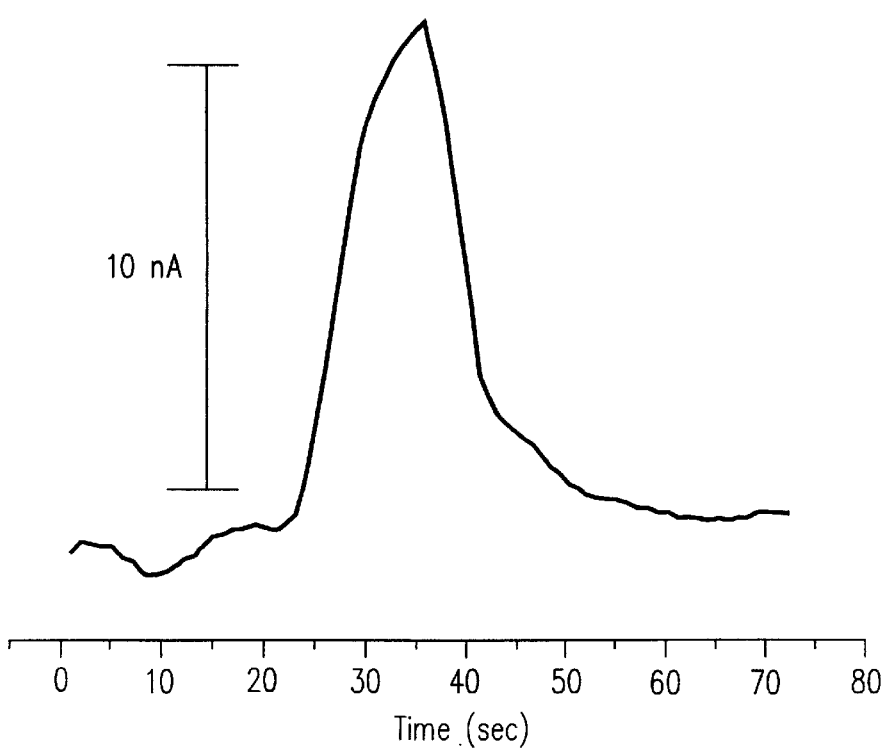
FIG. 7 shows the sinusoidal time domain response from 1 μM arginine at the fifth harmonic (10 Hz).

FIG. 7 shows the sinusoidal time domain response from 1 $\mu$M arginine at the fifth harmonic (10 Hz). This harmonic gave the highest signal/noise and a limit of detection (S/N=3) of 39 nM.

Figure 8:
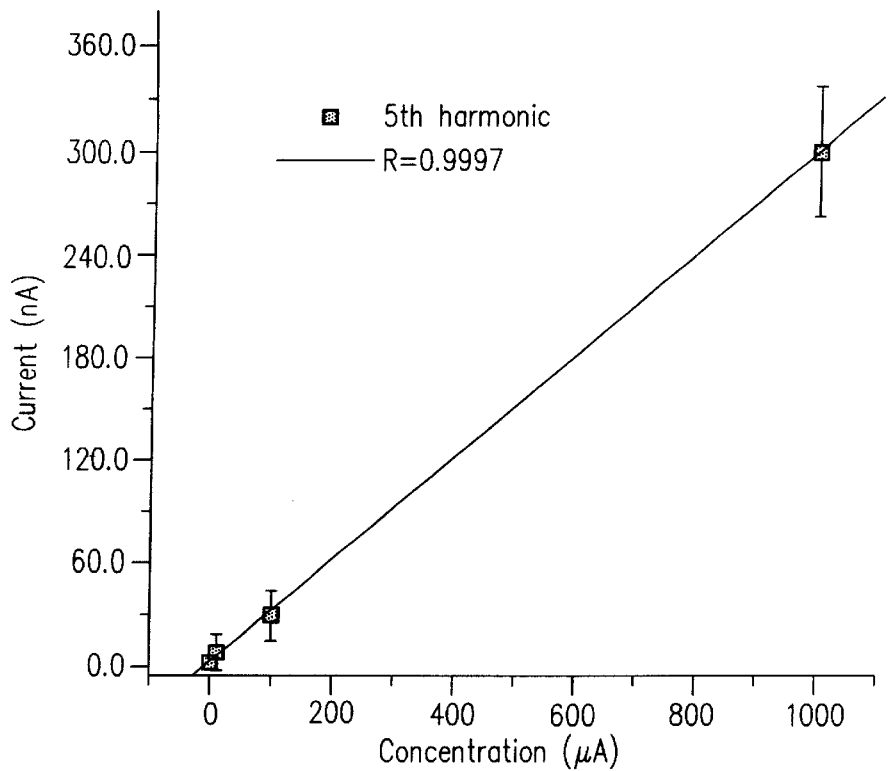
FIG. 8 demonstrates the linear dynamic range of various arginine concentrations.

FIG. 8 demonstrates the linear dynamic range of various arginine concentrations. Arginine concentrations of 1, 10, 100, and 1000 $\mu$M were injected into the flow injection analysis system. The magnitudes at the fifth harmonic (10 Hz) are plotted against the four different concentrations injected. This plot shows excellent linearity (R=0.9997) over three orders of magnitude at the fifth harmonic.

Figure 9:
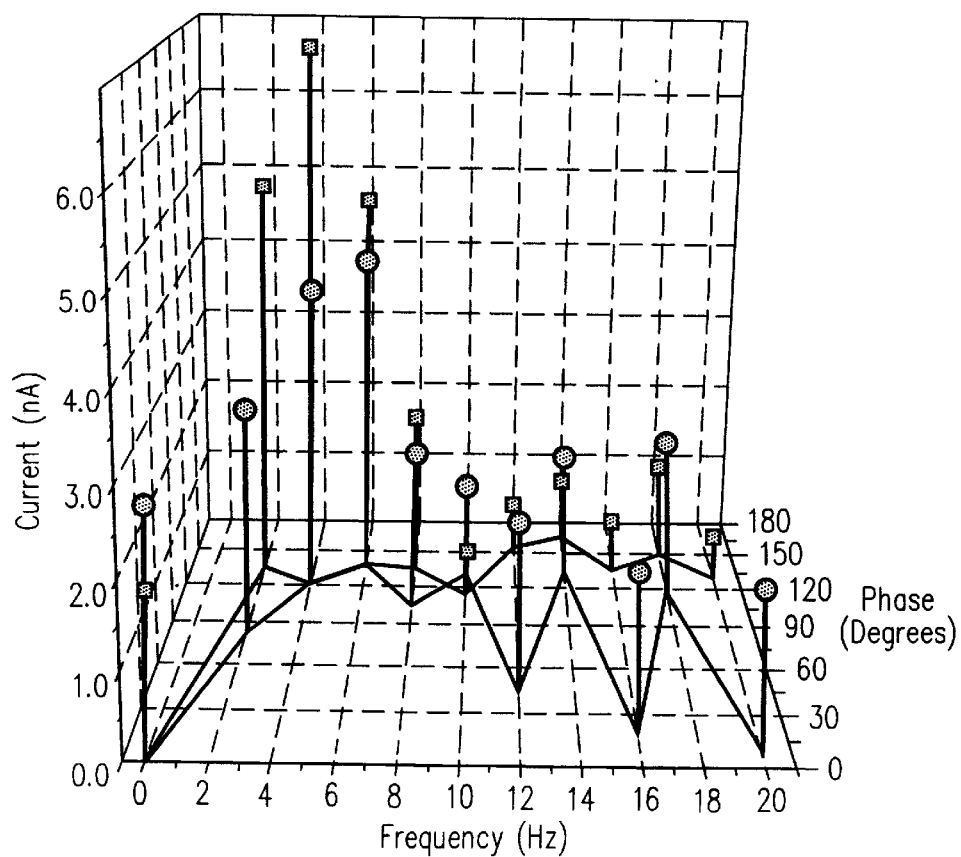
FIG. 9 shows the subtracted frequency spectra for asparagine and glutamine at a copper microelectrode. The squares represent 10 μM asparagines, while the circles represent 10 μM glutamine.

FIG. 9 shows the subtracted frequency spectra for asparagine and glutamine at a copper microelectrode. The squares represent 10 $\mu$M asparagines, while the circles represent 10 $\mu$M glutamine. The experimental conditions are the same as those used to generate FIG. 1.

FIGS. 10A and 10B show the sinusoidal time domain response of asparagine and glutamine at the sixth harmonic (12 Hz). FIG. 10A shows 10 $\mu$M asparagines, while FIG. 10B shows 10 $\mu$M glutamine. The sixth harmonic is where these two amino acids optimized phase angles are closest to 90 degrees apart. This harmonic gives the greatest selectivity between these two analytes. The limit of detection at this harmonic (S/N=3) for asparagine is 400 nM and 500 nM for glutamine.

FIG. 11 shows the background subtracted frequency domain spectrum for 10 $\mu$M Insulin B-chain. The same conditions as FIG. 1 were used.

Figure 12:
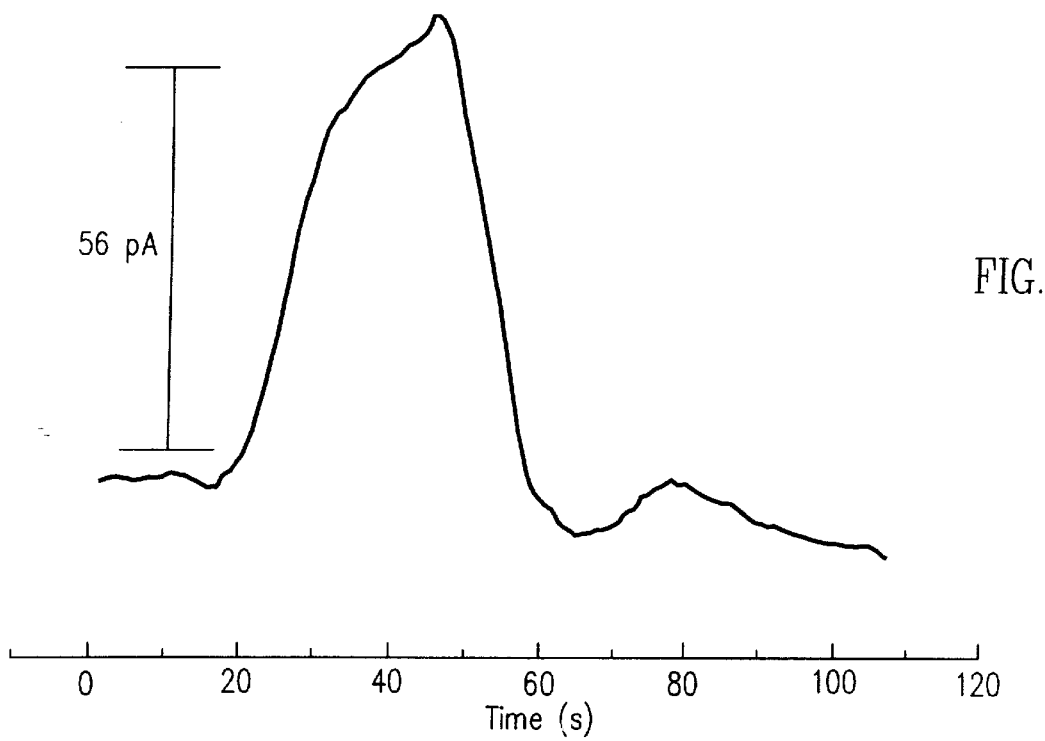
FIG. 12 shows the sinusoidal time domain component of insulin B-chain at the fourth harmonic (8 Hz).

FIG. 12 shows the sinusoidal time domain component of insulin B-chain at the fourth harmonic (8 Hz). The fourth harmonic gave the greatest signal/noise and a limit of detection (S/N=3) of 500 nM.

Figure 13:
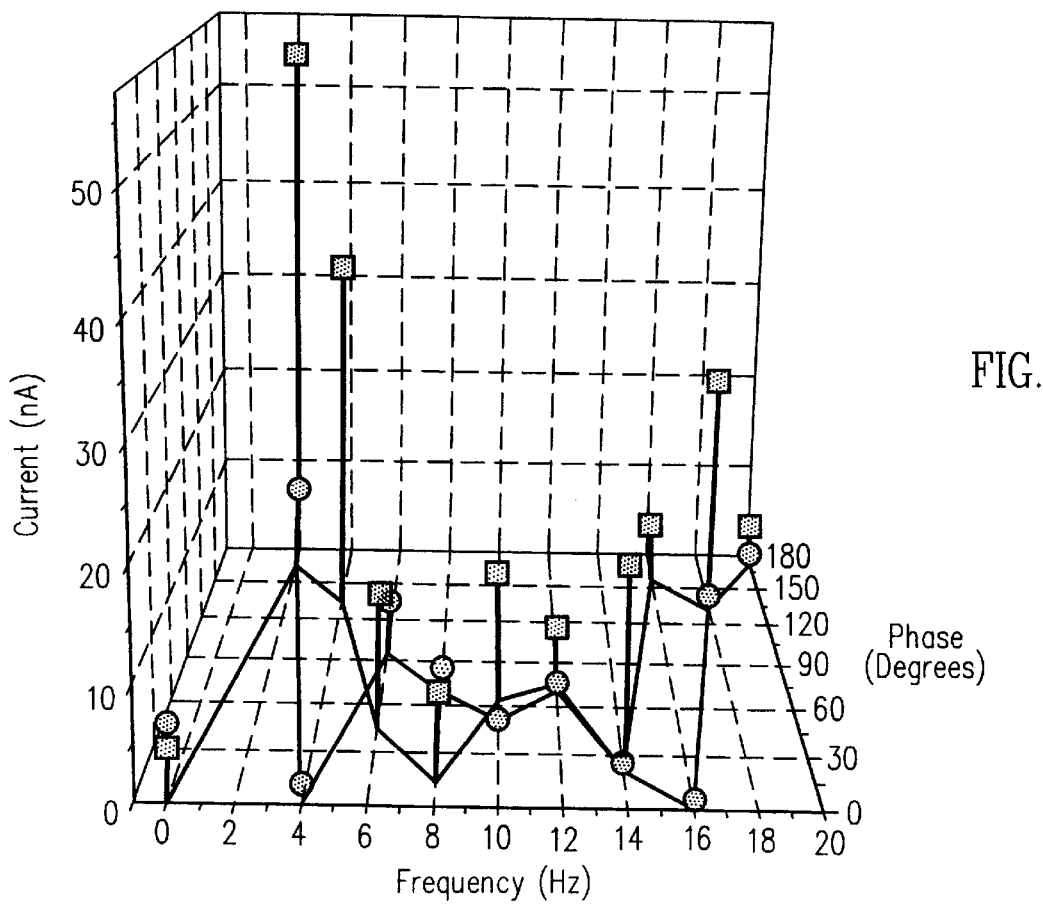
FIG. 13 shows the subtracted frequency spectra for Luteinizing Hormone-Releasing Hormone and Bradykinin at a copper microelectrode.

FIGS. 13 show the subtracted frequency spectra for Luteinizing Hormone-Releasing Hormone and Bradykinin at a copper microelectrode. FIG. 13 shows 10 $\mu$M Luteininzing Hormone, while FIG. 13 shows 10 $\mu$M Bradykinin. The experimental conditions are the same as FIG. 1.

FIGS. 14A and 14B show the time domain response of Bradykinin and Luteinizing Hormone-Releasing Hormone at the second harmonic (4 Hz), respectively. The optimized phase angles at the second harmonic were the most out of phase for these two peptides. This would allow the selective detection of these two analytes. The limit of detection for bradykinin at this harmonic (S/N=3) is 10 nM and 870 nM for Luteinizing Hormone.

FIGS. 15 show the background subtracted frequency domain response for Neurotensin and Substance P. FIG. 15 shows the response for 10 μM Neurotensin, while FIG. 15 shows the response for 10 μM Substance P. The experimental conditions are the same as FIG. 1.

Figures 16A, 16B:
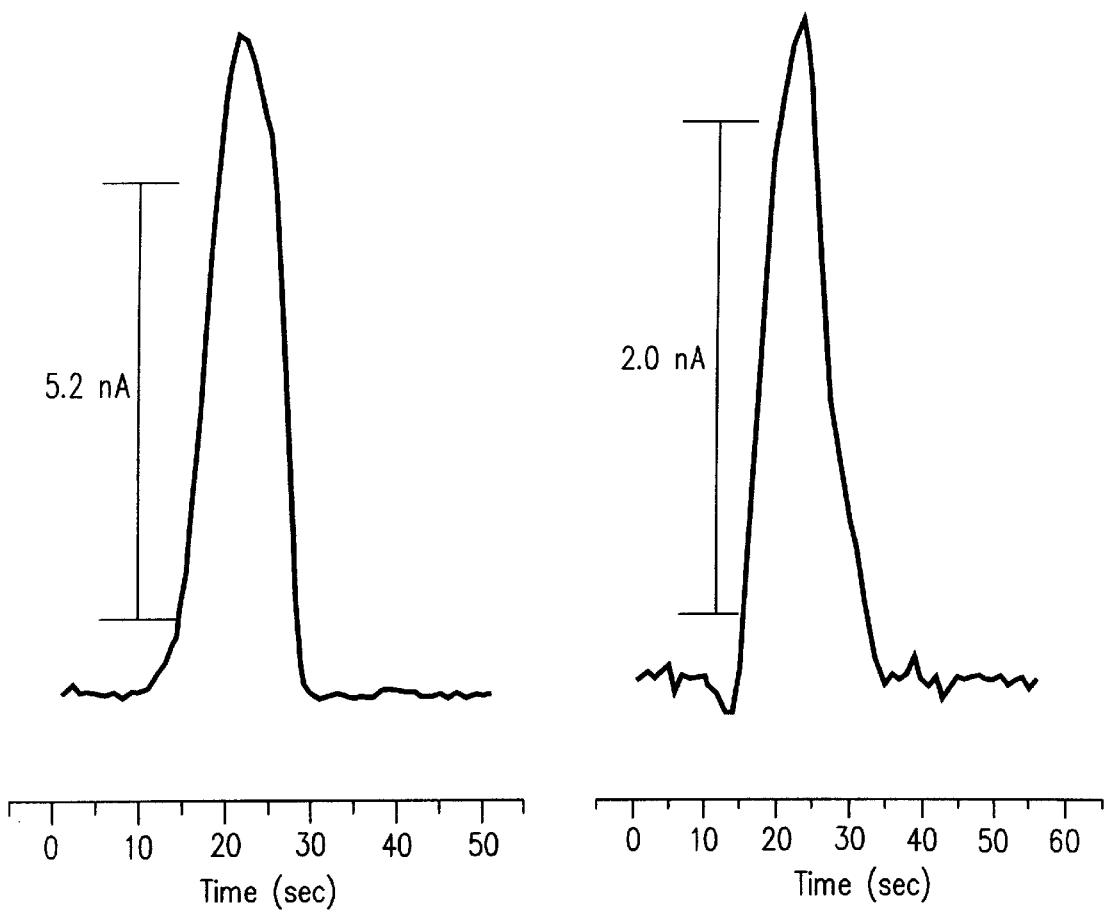
FIG. 16A and 16B show the time domain response of Neurotensin and Substance P, respectively, at the first harmonic (2 Hz).

FIGS. 16A and 16B show the time domain response of Neurotensin and Substance P, respectively, at the first harmonic (2 Hz). These two peptides are most out of phase with each other at the first harmonic. The limit of detection at this harmonic for neurotensin is 300 nM and 87 nM for substance P.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device for detecting a two or more analytes in a sample, said device comprising:
   a channel having affixed therein a binding partner for each of said two or more analytes, where the binding partners for each of said two or more analytes are located in different regions of said channel prior to sample introduction and said channel has a cross-sectional area small enough such that when analytes are released from said two or more binding partners into a fluid flowing through said channel, said analytes remain spatially segregated until they reach a detection point along said channel downstream from said binding partners; and
   a detector that detects said analytes within said channel at said detection point.

2. The device of claim 1, wherein said channel is a capillary tube.

3. The device of claim 2, wherein said capillary tube is a capillary electrophoresis tube.

4. The device of claim 1, wherein said channel is a channel etched in a surface.

5. The device of claim 4, wherein said channel is a channel etched in a glass surface.

6. The device of claim 1, wherein said channel has a cross-sectional area that provides a Renold's number (Re) of less than about 1.

7. The device of claim 1, wherein said channel has a cross-sectional diameter less than about 100 μm.

8. The device of claim 1, wherein said two or more target analytes comprise at least three different analytes.

9. The device of claim 1, wherein said binding partners are selected from the group consisting of antibodies, binding proteins, and nucleic acids.

10. The device of claim 9, wherein said binding partners are nucleic acids.

11. The device of claim 1, wherein said detector comprises an absorbance spectrometer.

12. The device of claim 1, wherein said detector comprises a sinusoidal voltammeter.

13. A kit for the detection of two or more target analytes in a fluid, said kit comprising a channel having affixed therein a binding partner for each of said two or more analytes, where the binding partners for each of said two or more analytes are located in different regions of said channel prior to sample introduction and said channel has a cross-sectional area small enough such that when analytes are released from said two or more binding partners into a fluid flowing through said channel, said analytes remain spatially segregated until they reach a detection point in said channel downstream from said binding partners.

14. The kit of claim 13, wherein said kit comprises a plurality of said channel.

15. The kit of claim 14, wherein the channels comprising the plurality of channel each have a unique collection of binding partners.

16. The kit of claim 14, wherein said channel is a capillary tube.

17. The kit of claim 16, said capillary tube is a capillary electrophoresis tube.

18. The kit of claim 14, wherein said channel is a channel etched in a surface.

19. The kit of claim 18, wherein said channel is a channel etched in a glass surface.

20. The kit of claim 14, wherein said channel has a cross-sectional area that provides a Renold's number (Re) of less than about 1.

21. The kit of claim 14, wherein said channel has a cross-sectional diameter less than about 100 μm.

22. The kit of claim 14, wherein said channel contains at least 3 different species of binding partner.

23. The kit of claim 14, wherein said binding partners are selected from the group consisting of antibodies, binding proteins, and nucleic acids.

24. The kit of claim 23, wherein said binding partners are nucleic acids.

* * * * *